(12) United States Patent
Kim et al.

(10) Patent No.: US 8,986,853 B2
(45) Date of Patent: Mar. 24, 2015

(54) RED PHOSPHORESCENT COMPOSITION AND ORGANIC ELECTROLUMINESCENT DEVICE USING THE SAME

(75) Inventors: Do Han Kim, Goyang-si (KR); Chun Gun Park, Seoul (KR); Jong-Kwan Bin, Geumdang2-ri (KR); Kyung Hoon Lee, Goyang-si (KR); Hyun-cheol Jeong, Gamdang-ri (KR); Dong-hee Yoo, Seoul (KR); Nam Sung Cho, Goyang-si (KR); Jong-Hyun Park, Seoul (KR); Tae han Park, Seoul (KR); Soon Wook Cha, Goyang-si (KR); Seung Jae Lee, Seoul (KR); In Bum Song, Uijeongbu-si (KR); Jung Keun Kim, Gimpo-si (KR)

(73) Assignee: LG Display Co., Ltd., Seoul (KR)

( * ) Notice: Subject to any disclaimer, the term of this patent is extended or adjusted under 35 U.S.C. 154(b) by 965 days.

(21) Appl. No.: 12/628,692

(22) Filed: Dec. 1, 2009

(65) Prior Publication Data

US 2010/0133524 A1    Jun. 3, 2010

(30) Foreign Application Priority Data

Dec. 1, 2008    (KR) .......................... 10-2008-120419

(51) Int. Cl.
| | | |
|---|---|---|
| H01L 51/54 | (2006.01) | |
| C09K 11/06 | (2006.01) | |
| H01L 51/00 | (2006.01) | |
| H05B 33/10 | (2006.01) | |
| C07F 15/00 | (2006.01) | |
| H01L 51/50 | (2006.01) | |

(52) U.S. Cl.
CPC ............ *H01L 51/0085* (2013.01); *C09K 11/06* (2013.01); *H05B 33/10* (2013.01); *C07F 15/0006* (2013.01); *C09K 2211/1007* (2013.01); *C09K 2211/1011* (2013.01); *C09K 2211/1029* (2013.01); *C09K 2211/185* (2013.01); *H01L 51/0081* (2013.01); *H01L 51/5016* (2013.01); *Y10S 428/917* (2013.01)
USPC .... 428/690; 428/917; 313/504; 257/E51.044; 252/301.16; 546/10

(58) Field of Classification Search
None
See application file for complete search history.

(56) References Cited

U.S. PATENT DOCUMENTS

2003/0042848 A1* 3/2003 Park et al. ..................... 313/503
2003/0072964 A1* 4/2003 Kwong et al. ................ 428/690

FOREIGN PATENT DOCUMENTS

CN    1589307      3/2005
EP    1783132 A1   5/2007

OTHER PUBLICATIONS

Office Action issued in corresponding Taiwanese Patent Application No. 098140911, mailed Dec. 25, 2012.
Office Action issued in corresponding Chinese Patent Application No. 200910226125.5, mailed Dec. 27, 2012.

* cited by examiner

*Primary Examiner* — Marie R. Yamnitzky
(74) *Attorney, Agent, or Firm* — Brinks Gilson & Lione

(57) ABSTRACT

A red phosphorescent compound includes a host material being capable of transporting an electron or a hole; and a dopant material represented by following Formula 1:

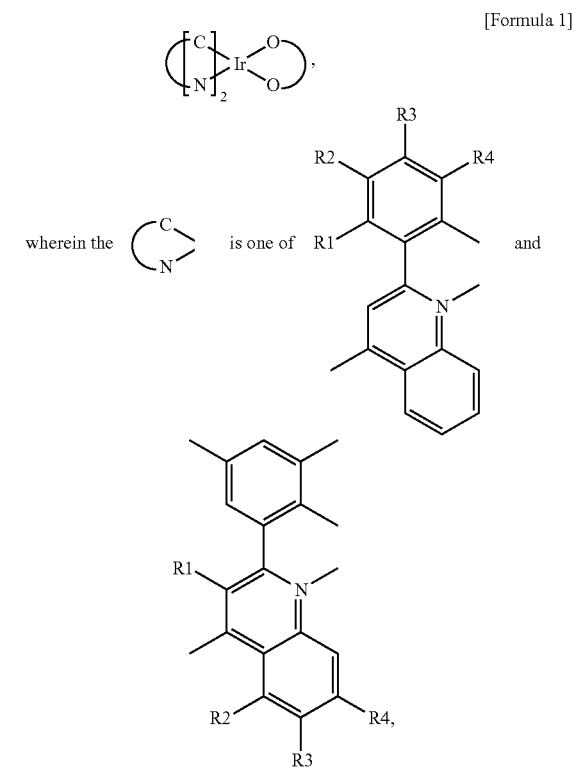

and each of R1 to R4 is one of the group consisting of hydrogen atom (H), C1 to C6 substituted or non-substituted alkyl group, C1 to C6 substituted or non-substituted alkoxy group, and halogen atom.

8 Claims, 2 Drawing Sheets

RED PHOSPHORESCENT COMPOSITION AND ORGANIC ELECTROLUMINESCENT DEVICE USING THE SAME

RELATED APPLICATIONS

The present application claims the benefit of Korean Patent Application No. 10-2008-0120419 filed in Korea on Dec. 1, 2008, which is hereby incorporated by reference in its entirety.

BACKGROUND

1. Field of the Disclosure

The present disclosure relates to a red phosphorescent compound and an organic electroluminescent device (OELD) and more particularly to a red phosphorescent compound having high color purity and high luminescent efficiency and an OELD using the red phosphorescent compound.

2. Discussion of the Related Art

Recently, the demand for a flat panel display device having a relatively large display area and a relatively small occupancy has increased. Among the flat panel display devices, an OELD has various advantages as compared to an inorganic electroluminescent device, a liquid crystal display device, a plasma display panel, and so on. The OELD device has excellent characteristics with respect to view angle, contrast ratio and so on. Also, since the OELD device does not require a backlight assembly, the OELD device has low weight and low power consumption. Moreover, the OELD device has advantages of a high response rate, a low production cost and so on.

In general, the OELD emits light by injecting electrons from a cathode and holes from an anode into an emission compound layer, combining the electrons with the holes, generating an exciton, and transforming the exciton from an excited state to a ground state. A flexible substrate, for example, a plastic substrate, can be used as a base substrate where elements are formed. The OELD has excellent characteristics of a view angel, a contrast ratio and so on. Also, since the OELD does not require a backlight assembly, the OELD has low weight and low power consumption. Moreover, the OELD has advantages of a high response rate, a low production cost, a high color purity and so on. The OELD can be operated at a voltage (e.g., 10V or below) lower than a voltage required to operate other display devices. In addition, the OELD is adequate to produce full-color images.

A general method for fabricating OELDs will be briefly explained below. First, an anode is formed on a substrate by depositing a transparent conductive compound, for example, indium-tin-oxide (ITO). Next, a hole injection layer (HIL) is formed on the anode. For example, the HIL may be formed of copper phthalocyanine (CuPC) and have a thickness of about 10 nm to about 30 nm. Next, a hole transporting layer (HTL) is formed on the HIL. For example, the HTL may be formed of 4,4'-bis[N-(1-naphthyl)-N-phenylamino]-biphenyl (NPB) and have a thickness of about 30 nm to about 60 nm. Next, an emitting compound layer (EML) is formed on the HTL. A dopant may be doped onto the EML. In a phosphorescent type, the EML may be formed of 4,4'-N,N'-dicarbazole-biphenyl (CBP) and have a thickness of about 30 nm to about 60 nm, and the dopant may includes one of iridium complex represented by following Formulas 1-1 to 1-3.

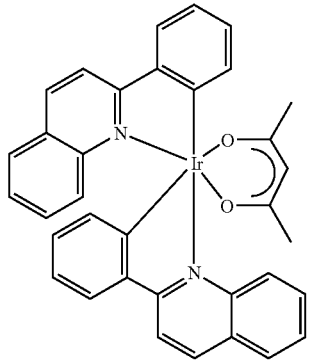

[Formula 1-1]

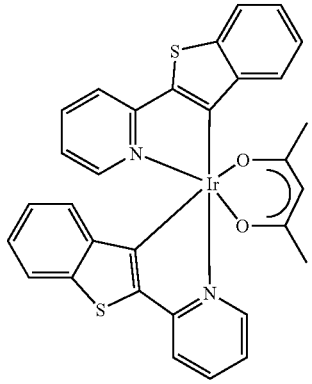

[Formula 1-2]

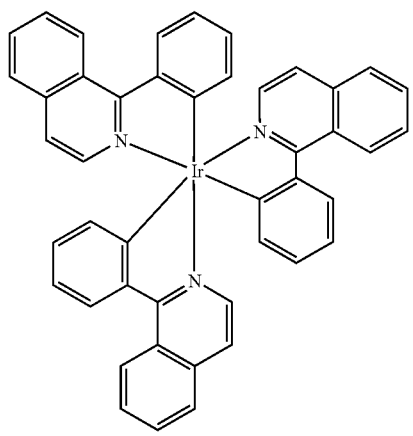

[Formula 1-3]

Next, an electron transporting layer (ETL) and an electron injection layer (EIL) are stacked on the EML. For example, the ETL may be formed of tris(8-hydroxy-quinolate)aluminum (Alq3). A cathode is formed on the EIL, and a passivation layer is formed on the cathode.

In the above structure, the EML produces red, green and blue colors such that the OELD can display full-color images. In an emitting compound, an exciton is generated by combining the electrons from a cathode and holes from an anode. The exciton includes a singlet exciton and a triplet exciton. The singlet exciton participates in a fluorescent type emission, while the triplet exciton participates in a phosphorescent type emission. The singlet exciton has a formation probability of about 25%, while the triplet exciton has a formation probability of about 75%. Accordingly, the phosphorescent type emission has luminescence efficiency greater than the fluorescent type emission.

In the phosphorescent compound, since a red phosphorescent compound has excellent luminescence efficiency as compared to a red fluorescent compound, the red phosphorescent compound has been widely developed and researched to improve an emission efficiency of the OELD. The phosphorescent compound is required to have high luminescence efficiency, high color purity, long life span, and so on. Particularly, as shown in FIG. 1, as the color purity of an OELD using a red phosphorescent material becomes higher (i.e. as the X index on CIE chromaticity coordinates increase), the relative spectral sensitivity of images from the OELD decreases. Accordingly, it is difficult to achieve high luminance efficiency of the OELD.

SUMMARY

A red phosphorescent compound includes a host material being capable of transporting an electron or a hole; and a dopant material represented by following Formula 1:

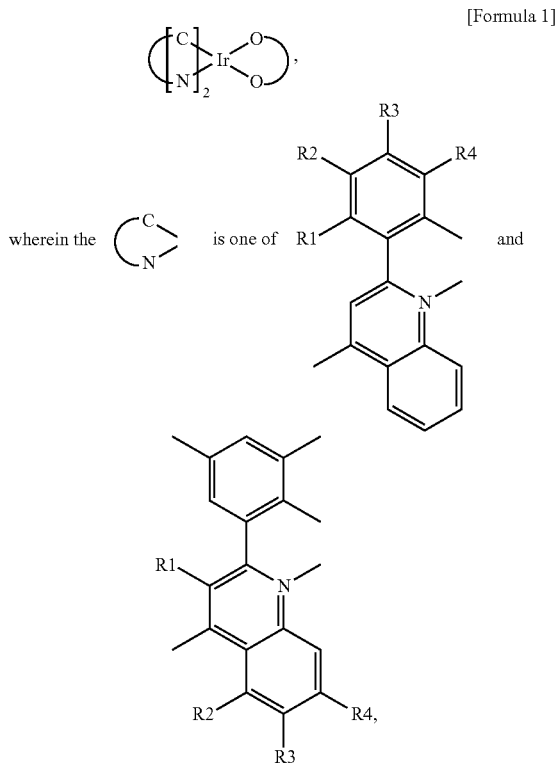

and each of R1 to R4 is one of the group consisting of hydrogen atom (H), C1 to C6 substituted or non-substituted alkyl group, C1 to C6 substituted or non-substituted alkoxy group, and halogen atom.

In another aspect, a red phosphorescent compound includes a host material being capable of transporting an electron or a hole; and a dopant material represented by following Formula 1:

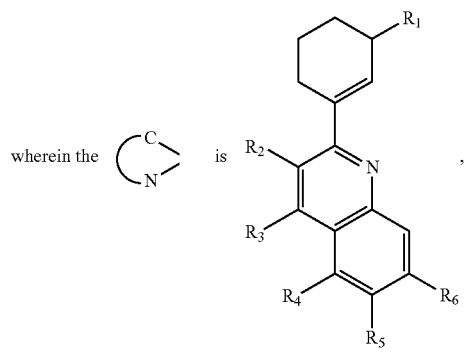

and R1 is one of C1 to C6 substituted or non-substituted alkyl group and C1 to C6 substituted or non-substituted alkoxy group, each of R2 to R6 is one of hydrogen atom (H), C1 to C6 substituted or non-substituted alkyl group, C1 to C6 substituted or non-substituted alkoxy group, halogen atom, trimethylsily group and tert-trifluoromethyl, and at least one of the R2 to R6 is one of C1 to C6 substituted or non-substituted alkyl group, C1 to C6 substituted or non-substituted alkoxy group, halogen atom, trimethylsily group and tert-trifluoromethyl.

In another aspect, an organic electroluminescent device includes a first substrate; a thin film transistor on the first substrate; a second substrate facing the first substrate; and an organic luminescent diode electrically connected to the thin film transistor and including a first electrode, a second electrode facing the first electrode and an organic emission layer disposed between the first and second electrodes, a red phosphorescent compound of the organic emission layer including a host material being capable of transporting an electron or a hole; and a dopant material represented by following Formula 1:

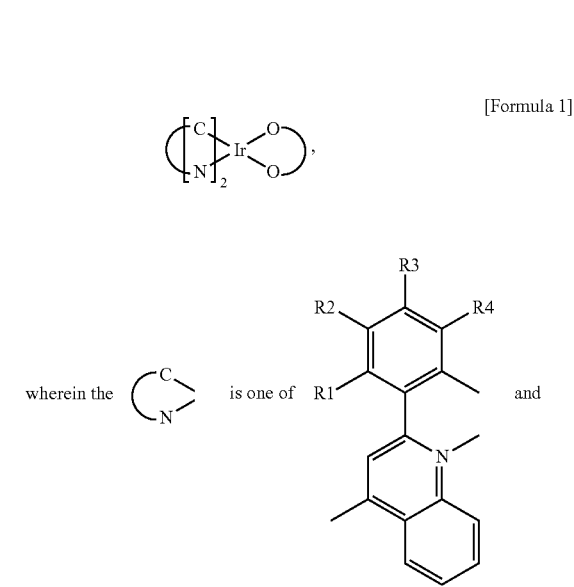

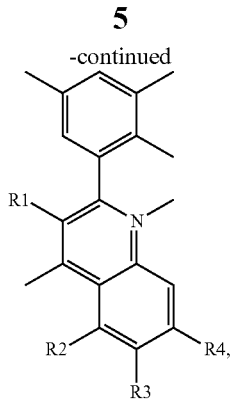

and each of R1 to R4 is one of the group consisting of hydrogen atom (H), C1 to C6 substituted or non-substituted alkyl group, C1 to C6 substituted or non-substituted alkoxy group, and halogen atom.

In another aspect, an organic electroluminescent device includes a first substrate; a thin film transistor on the first substrate; a second substrate facing the first substrate; and an organic luminescent diode electrically connected to the thin film transistor and including a first electrode, a second electrode facing the first electrode and an organic emission layer disposed between the first and second electrodes, a red phosphorescent compound of the organic emission layer including: a host material being capable of transporting an electron or a hole; and a dopant material represented by following Formula 1:

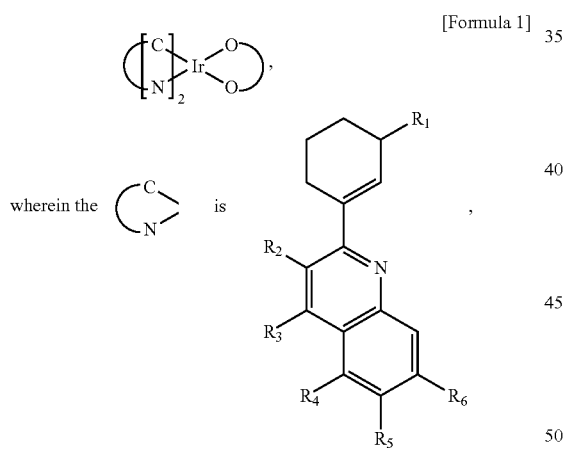

[Formula 1]

and R1 is one of C1 to C6 substituted or non-substituted alkyl group and C1 to C6 substituted or non-substituted alkoxy group, each of R2 to R6 is one of hydrogen atom (H), C1 to C6 substituted or non-substituted alkyl group, C1 to C6 substituted or non-substituted alkoxy group, halogen atom, trimethylsily group and tert-trifluoromethyl, and at least one of the R2 to R6 is one of C1 to C6 substituted or non-substituted alkyl group, C1 to C6 substituted or non-substituted alkoxy group, halogen atom, trimethylsily group and tert-trifluoromethyl.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE EXEMPLARY EMBODIMENTS

Figure 1:
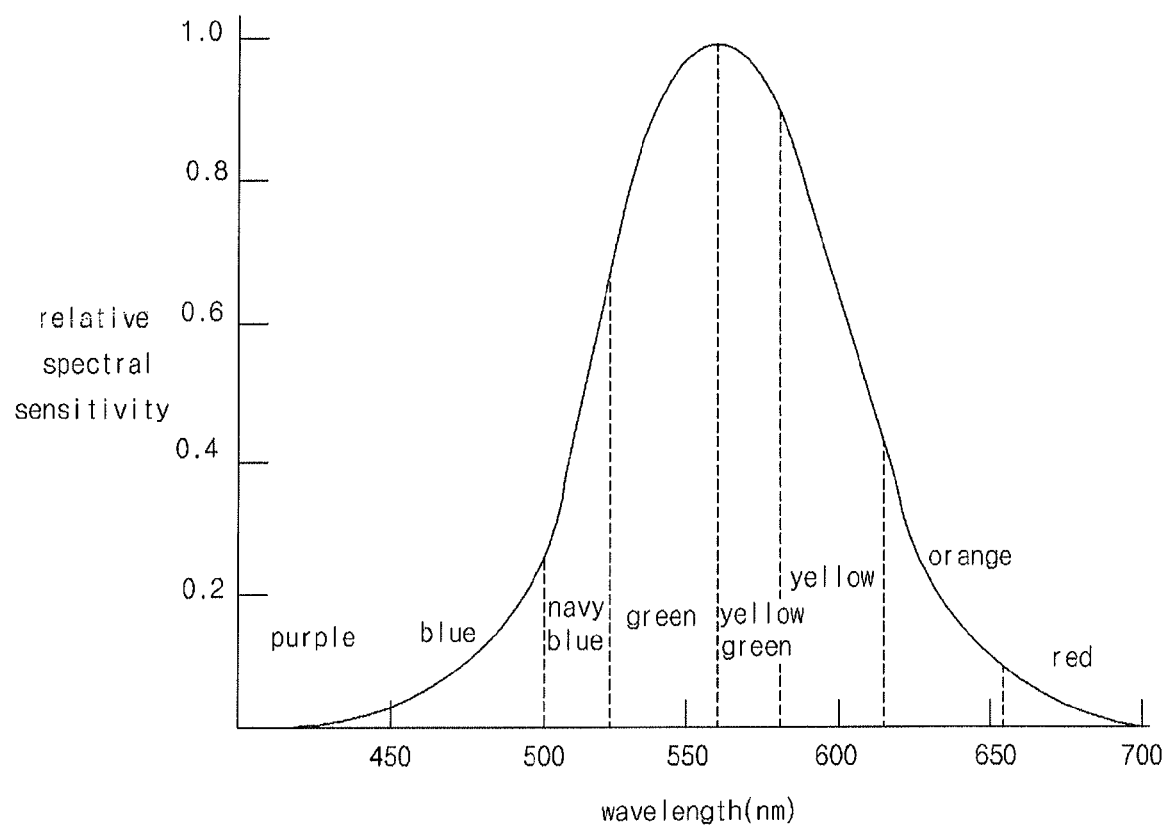
FIG. 1 is a graph showing a relation of a color purity and a visible degree.

Reference will now be made in detail to the preferred embodiments, examples of which are illustrated in the accompanying drawings.

-First Embodiment-

A red phosphorescent compound according to the first embodiment of the present invention includes a methyl group. Namely, in the red phosphorescent compound of the first embodiment of the present invention, a fourth position of a phenylquinoline ligand of an iridium (Ir) complex is substituted by the methyl group to improve a steric hindrance effect of the ligand. A quench effect by a molecules interaction is prevented due to improved steric hindrance effect such that the red phosphorescent compound has high luminescent efficiency and high color purity. The red phosphorescent compound is represented by following Formula 2.

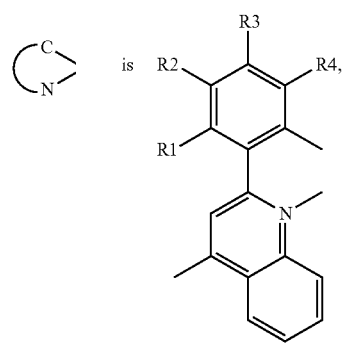

[formula 2]

In the above Formula 2, and each of R1 to R4 is selected from the group consisting of hydrogen atom (H), C1 to C6 substituted or non-substituted alkyl group, C1 to C6 substituted or non-substituted alkoxy group, and halogen atom. For example, the halogen atom includes fluorine (F), chlorine (Cl) and bromine (Br). The C1 to C6 alkyl group includes methyl, ethyl, n-propyl, i-propyl, n-butyl, i-butyl and t-butyl. The C1 to C6 alkoxy group includes methoxy, ethoxy, n-propoxy, i-propoxy, n-butoxy, i-butoxy and t-butoxy.

In addition, in the above formula 2,

as a right side structure of central iridium (Ir) is selected from the following Formulas 3-1 to 3-8. The structures of the Formulas 3-1 to 3-8 are 2,4-pentnedione, 2,2,6,6-tetramethylheptane-3,5-dione, 1,3-propanedione, 1,3-butanedione, 3,5-heptanedione, 1,1,1-trifluoro-2,4-pentanedione, 1,1,1,5,5,5-hexafluoro-2,4-pentanedione and 2,2-dimethyl-3,5-hexanedione, respectively.

[Formula 3-1]
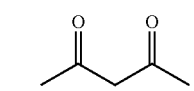

[Formula 3-2]
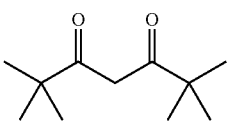

[Formula 3-3]

[Formula 3-4]
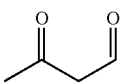

[Formula 3-5]
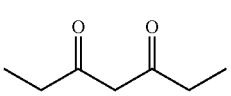

[Formula 3-6]
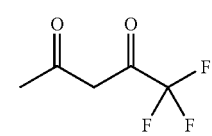

[Formula 3-7]
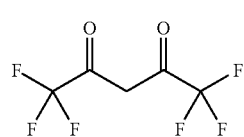

[Formula 3-8]
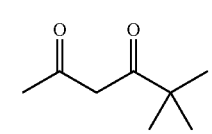

For example, the red phosphorescent compound represented by Formula 2 is selected from the following Formula 4.

[Formula 4]
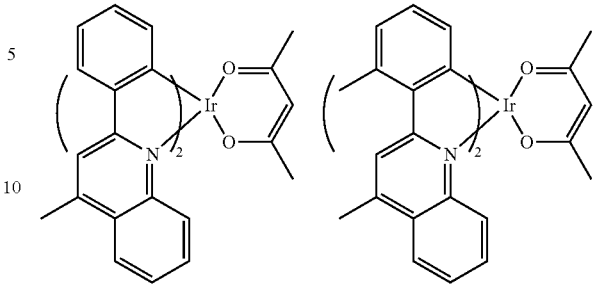
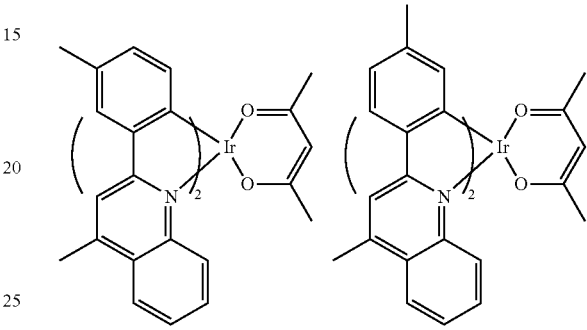
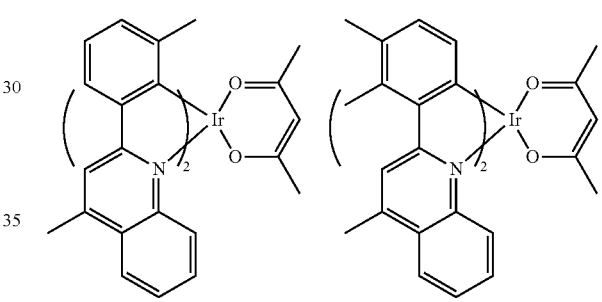
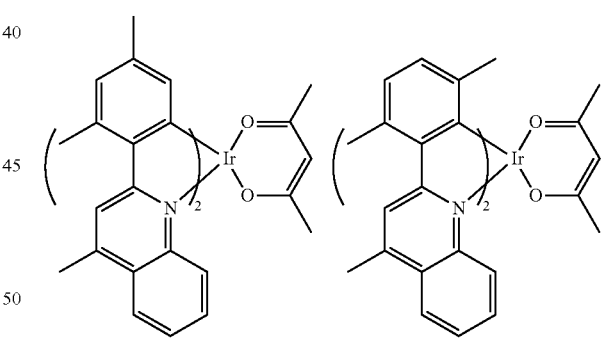
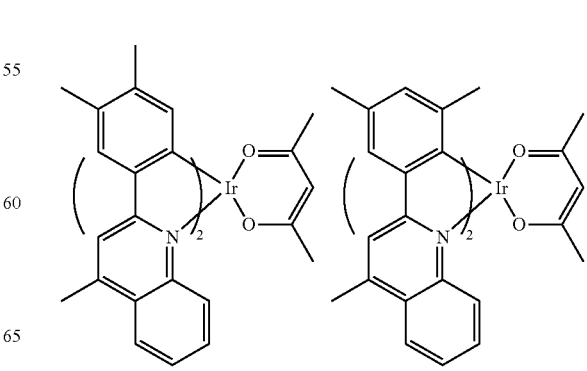

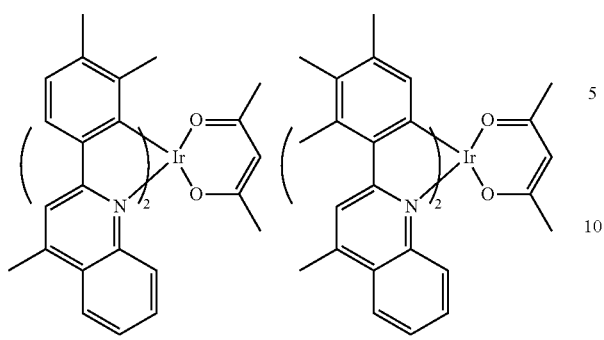
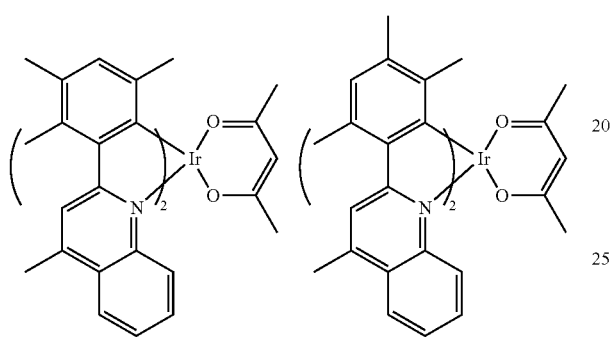
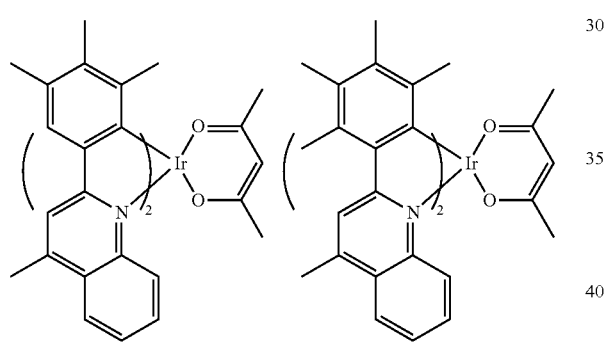
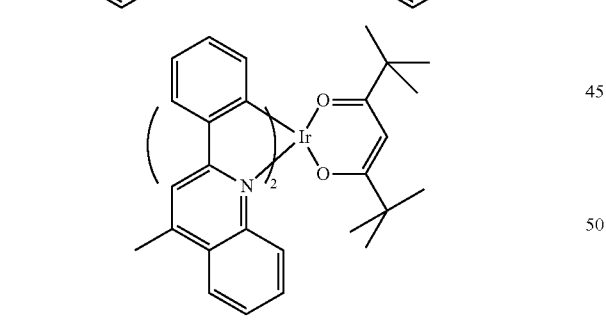
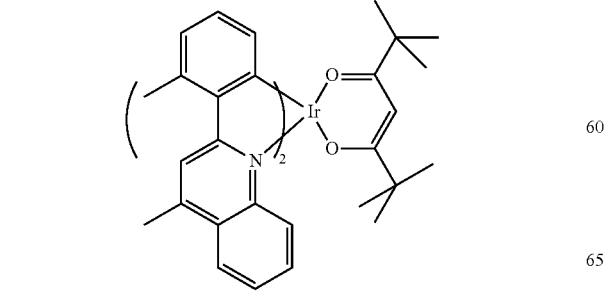
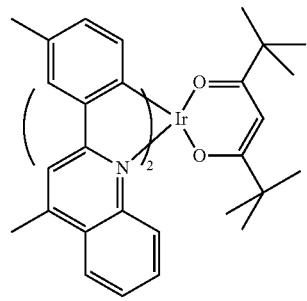
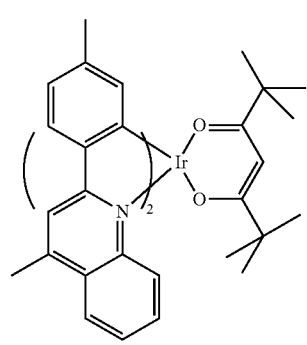
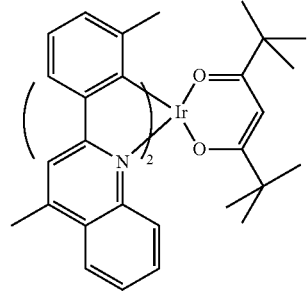
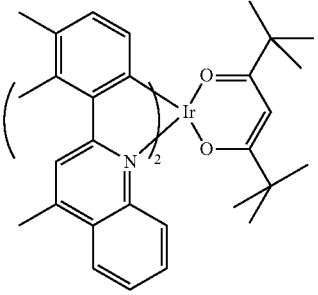
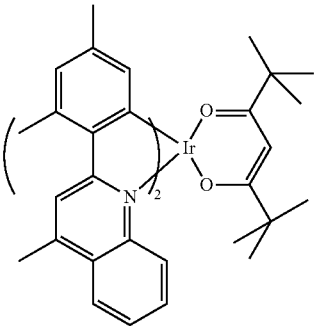

-continued
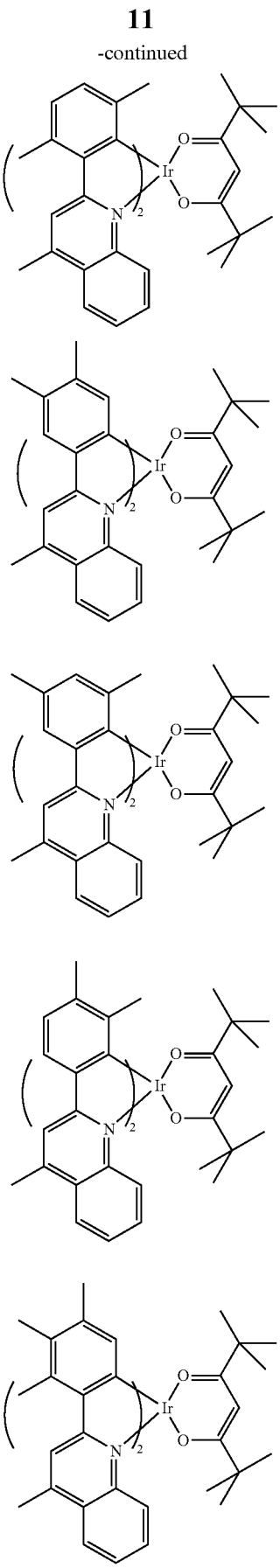
-continued
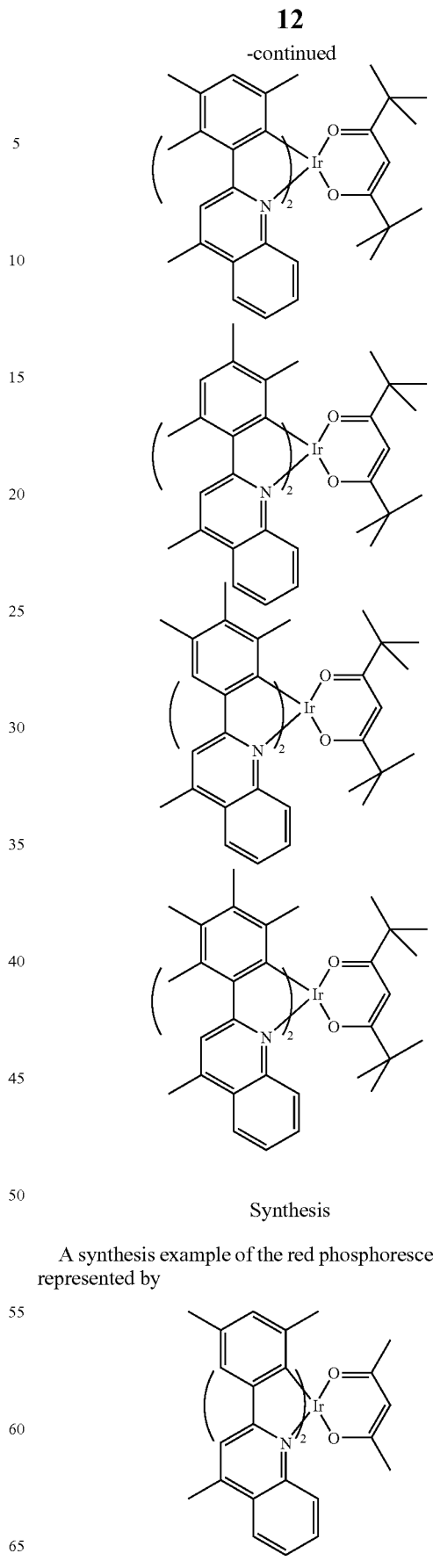
Synthesis
A synthesis example of the red phosphorescent compound represented by in the Formula 4 is explained. The red phosphorescent compound is iridium(III)bis{2-(3,5-dimethyl)-4-methylquinoline-N,C$^{2'}$}(2,4-pentanedionate-O,O).

1. Synthesis of 2-(3,5-dimethyl)-4-methylquinoline 2-(3,5-dimethyl)-4-methylquinoline is synthesized by following Reaction Formula 1.

[Reaction Formula 1]

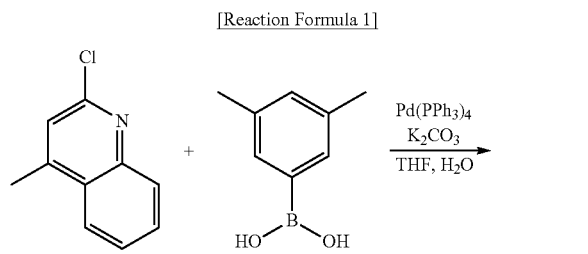

1-3,5 dimethylphenyl boric acid (12 mmol), 2-chloro-4-methylquinoline (10 mmol), tetrakis(triphenylphosphine)palladium(0) (0.5 mmol) and potassium carbonate (30 mmol) are put in a two-neck round-bottom flask and dissolved in tetrahydrofuran (THF) (60 mL) and distilled water (20 mL). Subsequently, the resulting solution is stirred in a bath under a temperature of about 100° C. for 6 hours. After completion of the reaction, THF are removed. The reaction mixture is extracted with dichloromethane and water, and then being distilled under reduced pressure. The resulting residence is filtered by silica gel column and distilled under reduced pressure again. Next, by re-crystallizing and filtering with dichloromethane and petroleum ether, 2-(3,5-dimethyl)-4-methylquinoline is yielded.

2. Synthesis of chloro-bridged Ir dimer complex

Chloro-bridged Ir dimer complex is synthesized by following Reaction Formula 2.

[Reaction Formula 2]

Iridium (III) chloride (5 mmol) and 2-(3,5-dimethyl)-4-methylquinoline (12 mmol) is put in a mixed solvent (40 mL), where a ratio of 2-ethoxyethanol to distilled water is 3:1. The mixture is refluxed for 24 hours, and water is added thereto. The resulting solid is filtered and washed by methanol and petroleum ether to yield chloro-bridged Ir dimer complex.

3. Synthesis of iridium(III) bis{2-(3,5-dimethyl)-4-methylquinoline-N,C$^{2'}$}(2,4-pentanedionate-O,O)

Iridium(III) bis{2-(3,5-dimethyl)-4-methylquinoline-N,C$^{2'}$}(2,4-pentanedionate-O,O) is synthesized by following Reaction Formula 3.

[Reaction Formula 3]

Chloro-bridged Ir dimer complex (2 mmol), 2,4-pentanedione (6 mmol) and sodium carbonate (Na$_2$CO$_3$) (6 mmol) is put in 2-ethoxyethanol (30 mL), and is refluxed for 8 hours. The resulted mixture is cooled to a room temperature, and then distilled water is added thereto. The mixture is filtered. The resulted solid is dissolved in dichloromethane, and then is filtered by silica gel column. After dichloromethane is removed by being distilled under reduced pressure to obtain re-crystallized solid, the compound is yield by washing the re-crystallized solid using methanol and petroleum ether.

Hereinafter, a detailed description will be made of preferred examples associated with the OELD according to the present invention. More specifically, the examples relate to an OELD including an emission material layer which uses the red phosphorescent compound of Formula 2 as a dopant.

EXAMPLES

Example 1

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), 4,4'-bis[N-(1-naphthyl)-N-phenylamino]-biphenyl (NPD) (about 400 angstroms), an emitting layer (about 200 angstroms) including aluminum(III) bis(2-methyl-8-quinolinato)-4-phenylphenolate (BAlq) and

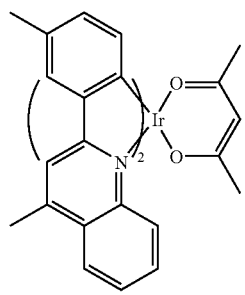

in the above Formula 4 as a dopant (about 5 weight %), Alq3 (about 300 angstroms), fluorolithium (LiF) (about 5 angstroms) and aluminum (Al) (about 1000 angstroms) are sequentially formed on the ITO layer such that an OELD is fabricated.

The OELD produces a brightness of 1682 cd/m² at an electric current of 0.9 mA and a voltage of 6.2 V. At this time, the X index and Y index of CIE color coordinates are 0.641 and 0.357, respectively.

Example 2

An ITO layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including BAlq and

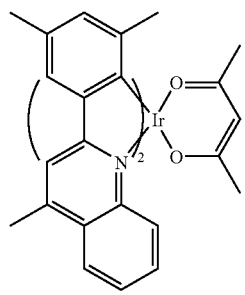

in the above Formula 4 as a dopant (about 5 weight %), Alq3 (about 300 angstroms), LiF (about 5 angstroms) and Al (about 1000 angstroms) are sequentially formed on the ITO layer such that an OELD is fabricated.

The OELD produces a brightness of 1850 cd/m² at an electric current of 0.9 mA and a voltage of 6.0 V. At this time, the X index and Y index of CIE color coordinates are 0.642 and 0.357, respectively.

Example 3

An ITO layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including BAlq and

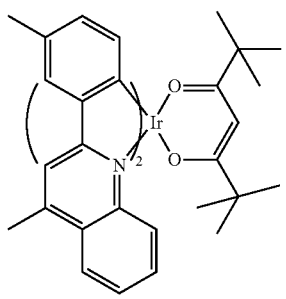

in the above Formula 4 as a dopant (about 5 weight %), Alq3 (about 300 angstroms), LiF (about 5 angstroms) and Al (about 1000 angstroms) are sequentially formed on the ITO layer such that an OELD is fabricated.

The OELD produces a brightness of 1947 cd/m² at an electric current of 0.9 mA and a voltage of 5.9 V. At this time, the X index and Y index of CIE color coordinates are 0.644 and 0.354, respectively.

Example 4

An ITO layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including BAlq and

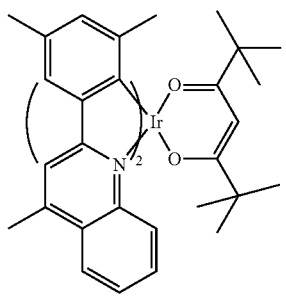

in the above Formula 4 as a dopant (about 5 weight %), Alq3 (about 300 angstroms), LiF (about 5 angstroms) and Al (about 1000 angstroms) are sequentially formed on the ITO layer such that an OELD is fabricated.

The OELD produces a brightness of 2243 cd/m² at an electric current of 0.9 mA and a voltage of 5.8 V. At this time, the X index and Y index of CIE color coordinates are 0.644 and 0.353, respectively.

Comparative Example 1

An ITO layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including BAlq and $(btp)_2Ir(acac)$ represented by following Formula 5-5 as a dopant (about 7 weight %), Alq3 (about 300 angstroms), LiF (about 5 angstroms) and Al (about 1000 angstroms) are sequentially formed on the ITO layer such that an OELD is fabricated.

The OELD produces a brightness of 780 cd/m² at an electric current of 0.9 mA and a voltage of 5.7 V. At this time, the X index and Y index of CIE color coordinates are 0.659 and 0.329, respectively.

Herein, CuPC, NPD, BAlq, Alq3 and $(btp)_2Ir(acac)$ are represented by following Formulas 5-1 to 5-5, respectively.

[Formula 5-1]

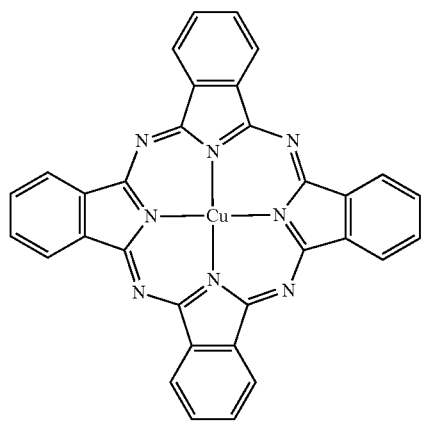

[Formula 5-2]

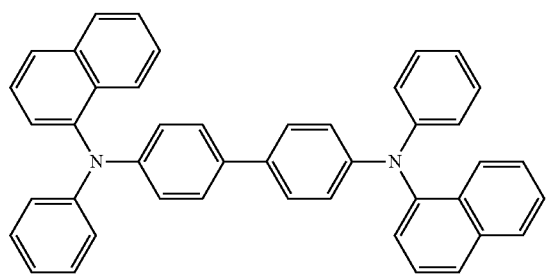

[Formula 5-3]

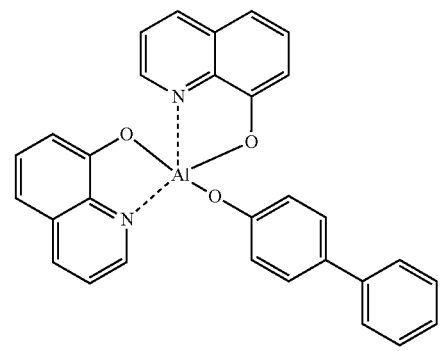

[Formula 5-4]

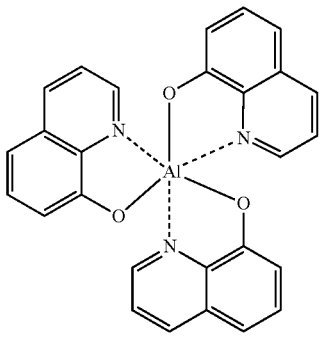

[Formula 5-5]

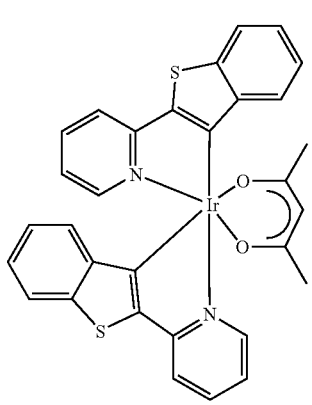

BAlq as a host is used for an emission material layer. However, the emission material layer may be formed of other materials. For example, Al metallic complex, zinc (Zn) metallic complex or CBP may be used for the emission material layer. CBP is a carbazole derivatives, such as 4-4'-N—N'-dicarbazole-1-1'-biphenyl, and represented by the above Formula 6. For example, the dopant is added into a host material by about 0.1 to 50 weight % with respect to a total weight of the emitting layer.

[Formula 6]

A ligand of the Al metallic complex or the Zn metallic complex may be selected from quinolinyl, biphenynyl, isoquinolinyl, phenylnyl, methylquinolinyl, dimethylquinolinyl, and dimethyl isoquinolinyl.

The OELD fabricated in Examples 1 to 4 and Comparative Example 1 is evaluated for efficiency, brightness, and so on. A voltage has a dimension of [V], an electric current has a dimension of [mA], a brightness has a dimension of [cd/m2], a current efficiency has a dimension of [cd/A], a power efficiency has a dimension of [lm/W], an internal quantum efficiency has a dimension of [%]. The evaluated results are shown in Table 1.

TABLE 1

| | voltage | Electric current | Brightness | Current efficiency | Power efficiency | Internal quantum efficiency | CIE (X) | CIE (Y) |
|---|---|---|---|---|---|---|---|---|
| Ex. 1 | 6.2 | 0.9 | 1682 | 16.82 | 8.5 | 16 | 0.641 | 0.357 |
| Ex. 2 | 6.0 | 0.9 | 1850 | 18.50 | 9.7 | 17 | 0.642 | 0.357 |
| Ex. 3 | 5.9 | 0.9 | 1947 | 19.47 | 1.4 | 19 | 0.644 | 0.354 |
| Ex. 4 | 5.8 | 0.9 | 2243 | 22.43 | 12.1 | 20 | 0.644 | 0.353 |
| Com. Ex. 1 | 7.5 | 0.9 | 780 | 7.80 | 3.3 | 10 | 0.659 | 0.329 |

As shown in Table 1, the OELD in Examples 1 to 4 has high color purity and high internal quantum efficiency. Accordingly, the OELD according to the present invention has improved luminescence efficiency. As a result, when the red phosphorescent compound of the present invention as a dopant for an emission material layer of an OELD, the OELD has high color purity, high brightness and high luminescence efficiency. The OELD can be driven by a relatively low power, power consumption can be reduced.

-Second Embodiment-

A red phosphorescent compound according to the second embodiment of the present invention includes a methyl group. Namely, in the red phosphorescent compound of the second embodiment of the present invention, a fourth position of a phenylquinoline ligand of an iridium (Ir) complex is substituted by the methyl group to improve a steric hindrance effect of the ligand. A quench effect by a molecules interaction is prevented due to improved steric hindrance effect such that the red phosphorescent compound has high luminescent efficiency and high color purity. The red phosphorescent compound is represented by following Formula 7.

[Formula 7]

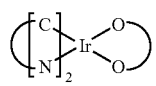

In the above Formula 7,

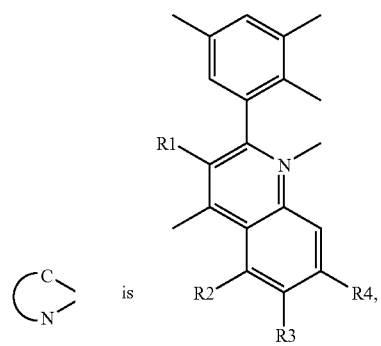

and each of R1 to R4 is selected from the group consisting of hydrogen atom (H), C1 to C6 substituted or non-substituted alkyl group, C1 to C6 substituted or non-substituted alkoxy group, and halogen atom. For example, the halogen atom includes fluorine (F), chlorine (Cl) and bromine (Br). The C1 to C6 alkyl group includes methyl, ethyl, n-propyl, i-propyl, n-butyl, i-butyl and t-butyl. The C1 to C6 alkoxy group includes methoxy, ethoxy, n-propoxy, i-propoxy, n-butoxy, i-butoxy and t-butoxy.

In addition, in the above formula 7,

as a right side structure of central iridium (Ir) is selected from the above Formulas 3-1 to 3-8. The structures of the above Formulas 3-1 to 3-8 are 2,4-pentanedione, 2,2,6,6-tetramethylheptane-3,5-dione, 1,3-propanedione, 1,3-butanedione, 3,5-heptanedione, 1,1,1-trifluoro-2,4-pentanedione, 1,1,1,5,5,5-hexafluoro-2,4-pentanedione and 2,2-dimethyl-3,5-hexanedione, respectively.

For example, the red phosphorescent compound represented by Formula 7 is selected from the following Formula 8.

[Formula 8]

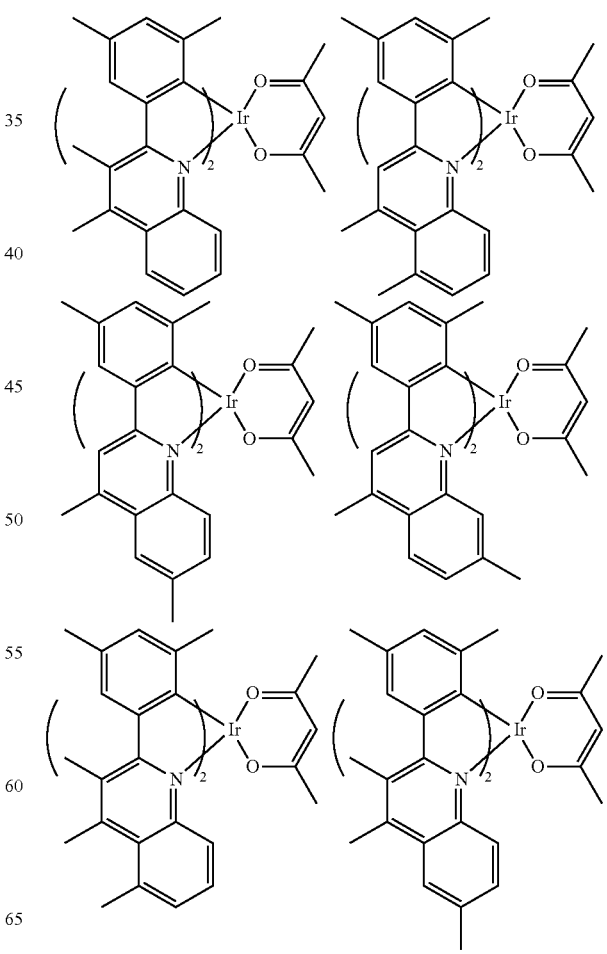

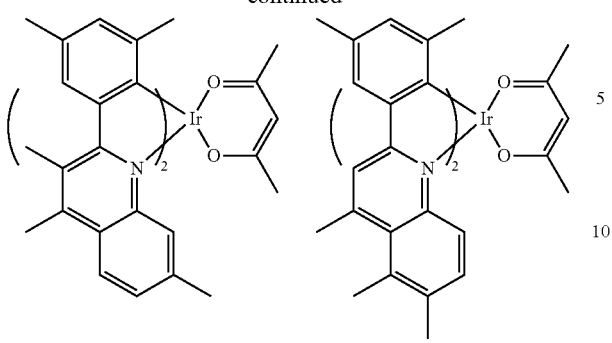
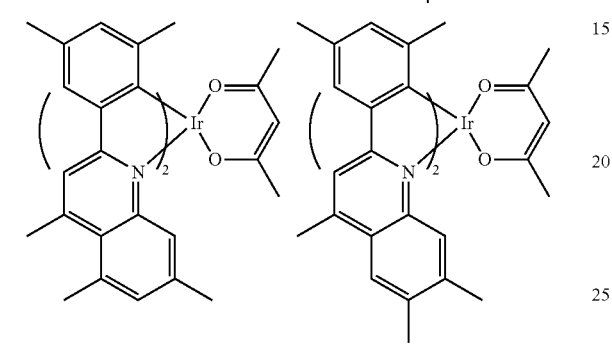
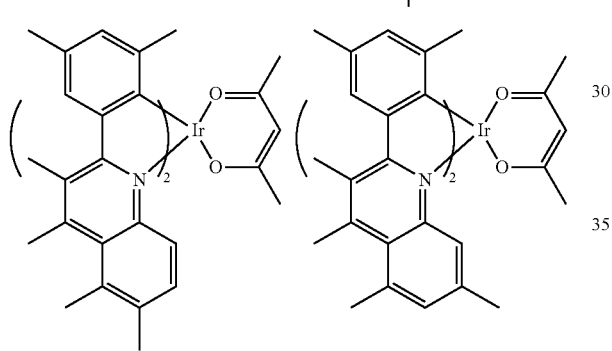
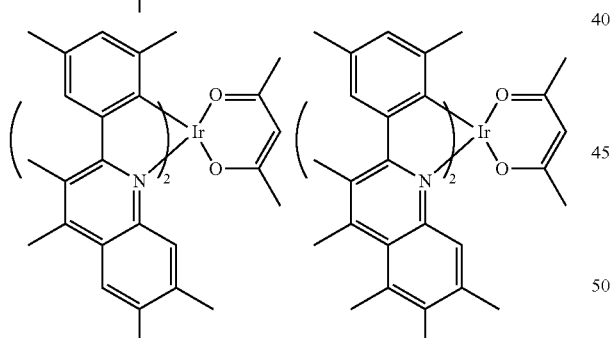
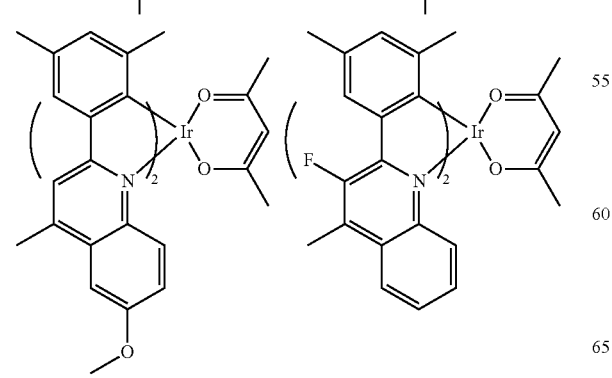
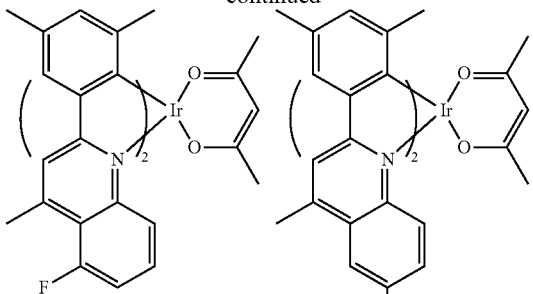
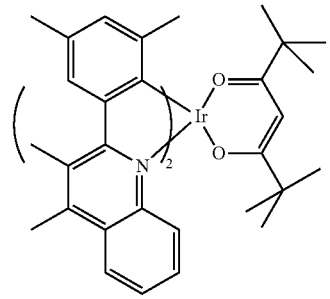
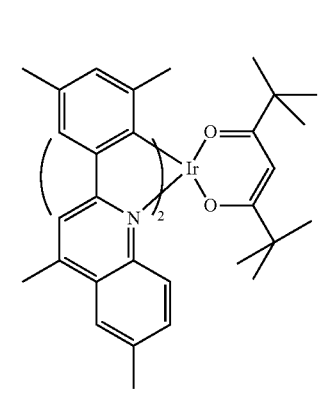
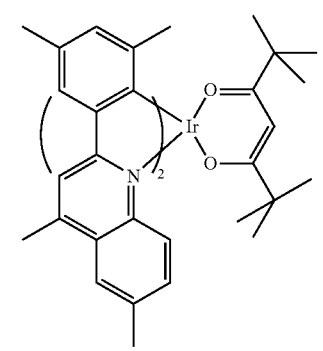
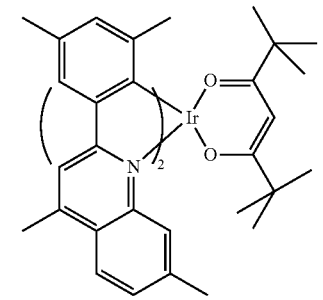

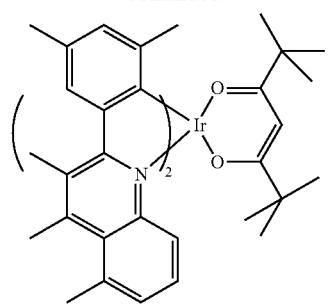
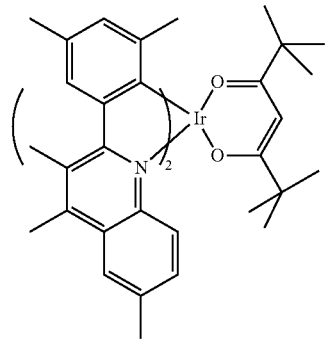
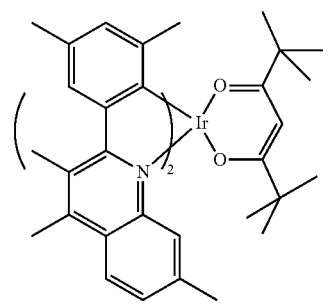
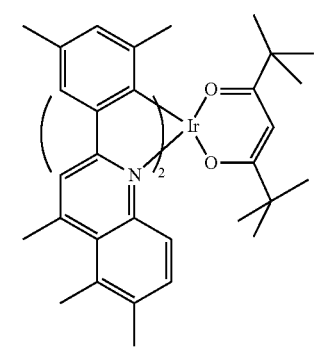
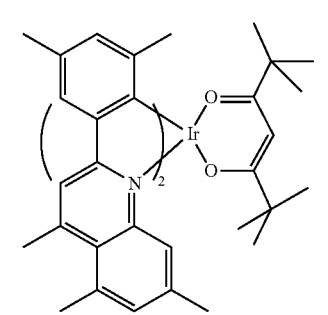
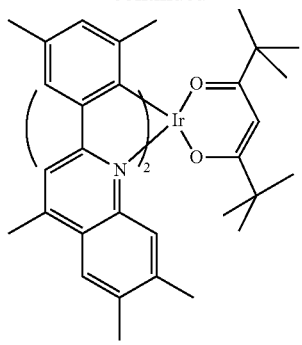
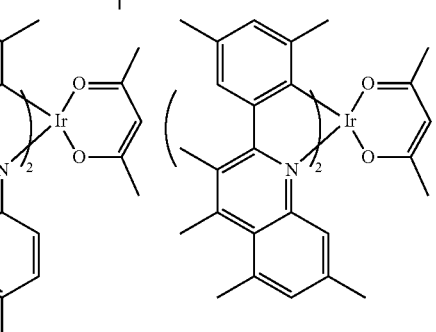
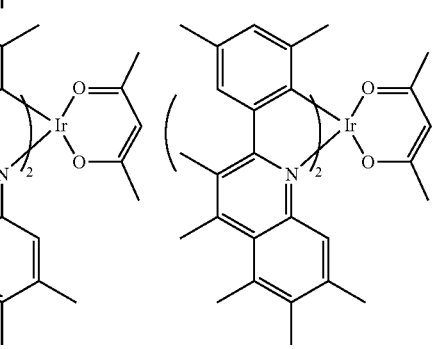
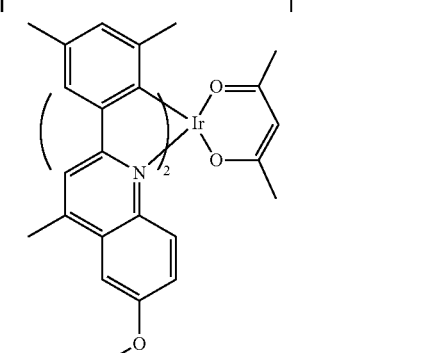
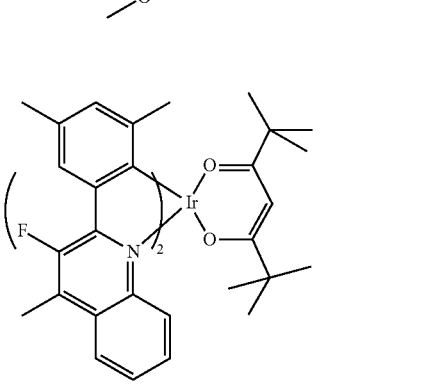

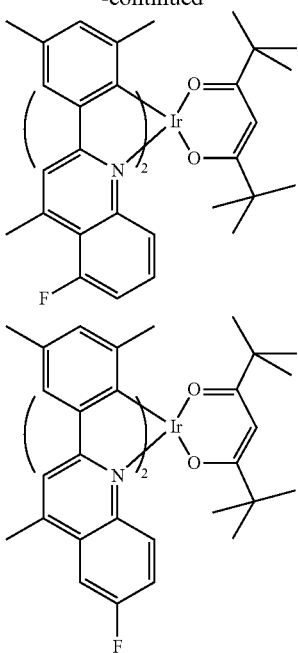

Synthesis

A synthesis example of the red phosphorescent compound represented by

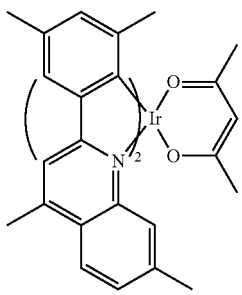

in the Formula 8 is explained. The red phosphorescent compound is iridium(III)bis{2-(3,5-dimethyl)-4,7-dimethylquinoline-N,$C^{2'}$}(2,4-pentanedionate-0,0).

1. Synthesis of 2-(3,5-dimethyl)-4,7-dimethylquinoline 2-(3,5-dimethyl)-4,7-dimethylquinoline is synthesized by following Reaction Formula 4.

[Reaction Formula 4]

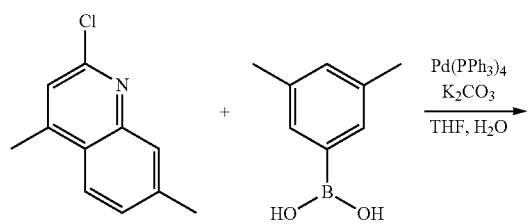

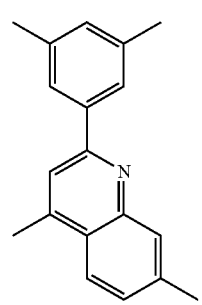

3,5-dimethylphenyl boric acid (12 mmol), 2-chloro-4,7-dimethylquinoline (10 mmol), tetrakis(triphenylphosphine)palladium(0) (0.5 mmol) and potassium carbonate (30 mmol) are put in a two-neck round-bottom flask and dissolved in tetrahydrofuran (THF) (60 mL) and distilled water (20 mL). Subsequently, the resulting solution is stirred in a bath under a temperature of about 100° C. for 6 hours. After completion of the reaction, THF are removed. The reaction mixture is extracted with dichloromethane and water, and then being distilled under reduced pressure. The resulting residence is filtered by silica gel column and distilled under reduced pressure again. Next, by re-crystallizing and filtering with dichloromethane and petroleum ether, 2-(3,5-dimethyl)-4,7-dimethylquinoline is yielded.

2. Synthesis of chloro-bridged Ir dimer complex

Chloro-bridged Ir dimer complex is synthesized by following Reaction Formula 5.

[Reaction Formula 5]

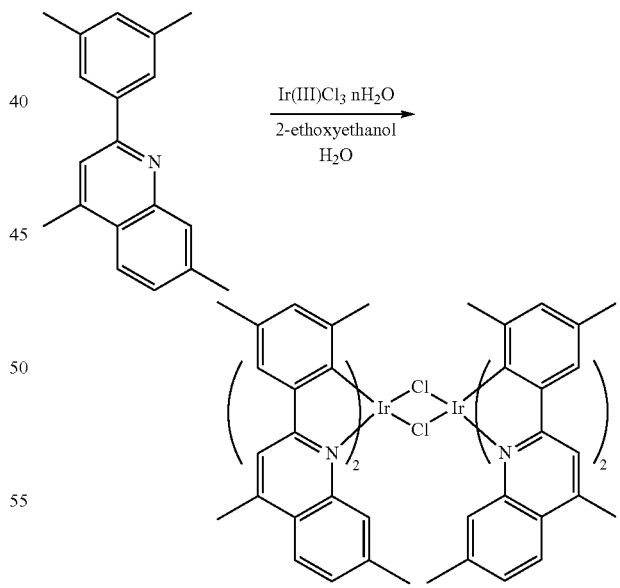

Iridium (III) chloride (5 mmol) and 2-(3,5-dimethyl)-4,7-dimethylquinoline (12 mmol) is put in a mixed solvent (40 mL), where a ratio of 2-ethoxyethanol to distilled water is 3:1. The mixture is refluxed for 24 hours, and water is added thereto. The resulting solid is filtered and washed by methanol and petroleum ether to yield chloro-bridged Ir dimer complex.

3. Synthesis of iridium(III) bis{2-(3,5-dimethyl)-4,7-dimethylquinoline-N,C$^{2'}$}(2,4-pentanedionate-0,0)

Iridium(III)bis{2-(3,5-dimethyl)-4,7-dimethylquinoline-N,C$^{2'}$}(2,4-pentanedionate-0,0) is synthesized by following Reaction Formula 6.

[Reaction Formula 6]

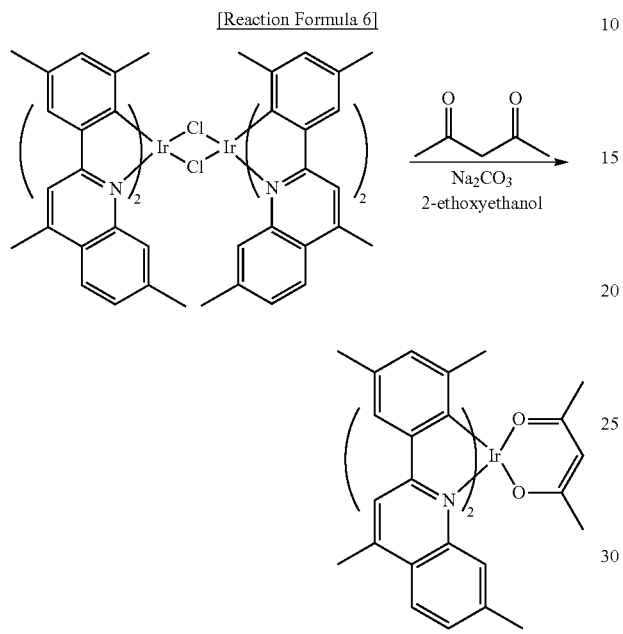

Chloro-bridged Ir dimer complex (2 mmol), 2,4-pentanedione (6 mmol) and sodium carbonate (Na$_2$CO$_3$) (6 mmol) is put in 2-ethoxyethanol (30 mL), and is refluxed for 8 hours. The resulted mixture is cooled to a room temperature, and then distilled water is added thereto. The mixture is filtered. The resulted solid is dissolved in dichloromethane, and then is filtered by silica gel column. After dichloromethane is removed by being distilled under reduced pressure to obtain re-crystallized solid, the compound is yield by washing the re-crystallized solid using methanol and petroleum ether.

Hereinafter, a detailed description will be made of preferred examples associated with the OELD according to the present invention. More specifically, the examples relate to an OELD including an emission material layer which uses the red phosphorescent compound of Formula 7 as a dopant.

EXAMPLES

Example 5

An indium-tin-oxide (ITO) layer is patterned on a substrate and washed such that an emission area of the ITO layer is 3 mm*3 mm. The substrate is loaded in a vacuum chamber, and the process pressure is adjusted to 1*10$^{-6}$ torr. CuPC (about 200 angstroms), 4,4'-bis[N-(1-naphthyl)-N-phenylamino]-biphenyl (NPD) (about 400 angstroms), an emitting layer (about 200 angstroms) including aluminum(III)bis(2-methyl-8-quinolinato)-4-phenylphenolate (BAlq) and

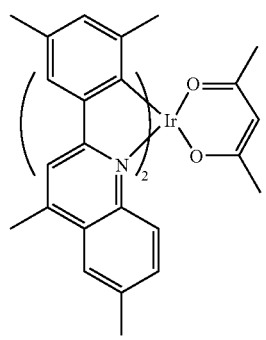

in the above Formula 8 as a dopant (about 5 weight %), Alq3 (about 300 angstroms), fluorolithium (LiF) (about 5 angstroms) and aluminum (Al) (about 1000 angstroms) are sequentially formed on the ITO layer such that an OELD is fabricated.

The OELD produces a brightness of 1843 cd/m$^2$ at an electric current of 0.9 mA and a voltage of 6.0 V. At this time, the X index and Y index of CIE color coordinates are 0.650 and 0.345, respectively.

Example 6

An indium-tin-oxide (ITO) layer is patterned on a substrate and washed such that an emission area of the ITO layer is 3 mm*3 mm. The substrate is loaded in a vacuum chamber, and the process pressure is adjusted to 1*10$^{-6}$ torr. CuPC (about 200 angstroms), NPD (about 400 angstroms), an emitting layer (about 200 angstroms) including BAlq and

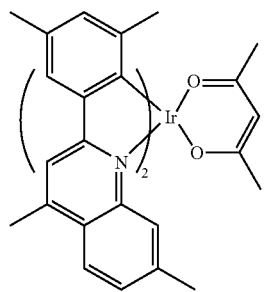

in the above Formula 8 as a dopant (about 5 weight %), Alq3 (about 300 angstroms), fluorolithium (LiF) (about 5 angstroms) and aluminum (Al) (about 1000 angstroms) are sequentially formed on the ITO layer such that an OELD is fabricated.

The OELD produces a brightness of 1872 cd/m$^2$ at an electric current of 0.9 mA and a voltage of 6.2 V. At this time, the X index and Y index of CIE color coordinates are 0.649 and 0.348, respectively.

Example 7

An indium-tin-oxide (ITO) layer is patterned on a substrate and washed such that an emission area of the ITO layer is 3 mm*3 mm. The substrate is loaded in a vacuum chamber, and the process pressure is adjusted to 1*10$^{-6}$ torr. CuPC (about 200 angstroms), NPD (about 400 angstroms), an emitting layer (about 200 angstroms) including BAlq and

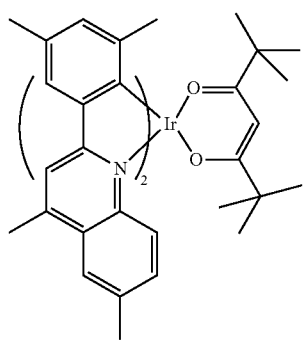

in the above Formula 8 as a dopant (about 5 weight %), Alq3 (about 300 angstroms), fluorolithium (LiF) (about 5 angstroms) and aluminum (Al) (about 1000 angstroms) are sequentially formed on the ITO layer such that an OELD is fabricated.

The OELD produces a brightness of 2092 cd/m² at an electric current of 0.9 mA and a voltage of 5.8 V. At this time, the X index and Y index of CIE color coordinates are 0.655 and 0.339, respectively.

Example 8

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including BAlq and

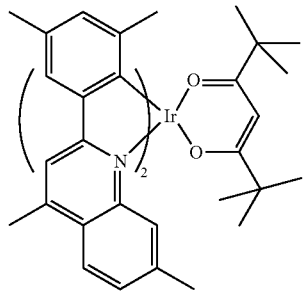

in the above Formula 8 as a dopant (about 5 weight %), Alq3 (about 300 angstroms), fluorolithium (LiF) (about 5 angstroms) and aluminum (Al) (about 1000 angstroms) are sequentially formed on the ITO layer such that an OELD is fabricated.

The OELD produces a brightness of 2054 cd/m² at an electric current of 0.9 mA and a voltage of 5.8 V. At this time, the X index and Y index of CIE color coordinates are 0.656 and 0.337, respectively.

Comparative Example 2

An ITO layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including BAlq and (btp)₂Ir(acac) represented by following Formula 5-5 as a dopant (about 7 weight %), Alq3 (about 300 angstroms), LiF (about 5 angstroms) and Al (about 1000 angstroms) are sequentially formed on the ITO layer such that an OELD is fabricated.

The OELD produces a brightness of 780 cd/m² at an electric current of 0.9 mA and a voltage of 5.7 V. At this time, the X index and Y index of CIE color coordinates are 0.659 and 0.329, respectively.

As mentioned above, BAlq as a host is used for an emission material layer. However, the emission material layer may be formed of other materials. For example, Al metallic complex, zinc (Zn) metallic complex or CBP may be used for the emission material layer. CBP is a carbazole derivatives, such as 4-4'-N—N'-dicarbazole-1-1'-biphenyl, and represented by the above Formula 6. For example, the dopant is added into a host material by about 0.1 to 50 weight %.

In addition, a ligand of the Al metallic complex or the Zn metallic complex may be selected from quinolinyl, biphenynyl, isoquinolinyl, phenylnyl, methylquinolinyl, dimethylquinolinyl, and dimethyl isoquinolinyl.

The OELD fabricated in Examples 5 to 8 and Comparative Example 2 is evaluated for efficiency, brightness, and so on. A voltage has a dimension of [V], an electric current has a dimension of [mA], a brightness has a dimension of [cd/m2], a current efficiency has a dimension of [cd/A], a power efficiency has a dimension of [lm/W], and an internal quantum efficiency has a dimension of [%]. The evaluated results are shown in Table 2.

TABLE 2

|  | voltage | Electric current | Brightness | Current efficiency | Power efficiency | Internal quantum efficiency | CIE (X) | CIE (Y) |
| --- | --- | --- | --- | --- | --- | --- | --- | --- |
| Ex. 1 | 6.0 | 0.9 | 1843 | 18.43 | 9.6 | 17 | 0.650 | 0.345 |
| Ex. 2 | 6.2 | 0.9 | 1872 | 18.72 | 9.5 | 17 | 0.649 | 0.348 |
| Ex. 3 | 5.8 | 0.9 | 2092 | 20.92 | 11.3 | 21 | 0.655 | 0.339 |
| Ex. 4 | 5.8 | 0.9 | 2054 | 20.54 | 11.1 | 20 | 0.656 | 0.337 |
| Com. Ex. 1 | 7.5 | 0.9 | 780 | 7.80 | 3.3 | 10 | 0.659 | 0.329 |

As shown in Table 2, the OELD in Examples 5 to 8 has high color purity and high internal quantum efficiency. Accordingly, the OELD according to the present invention has improved luminescence efficiency. As a result, when the red phosphorescent compound of the present invention as a dopant for an emission material layer of an OELD, the OELD has high color purity, high brightness and high luminescence efficiency. The OELD can be driven by a relatively low power, power consumption can be reduced.

-Third Embodiment-

A red phosphorescent compound according to the third embodiment of the present invention includes a cyclohexyl group. Namely, in the red phosphorescent compound of the third embodiment of the present invention, a second position of a phenylquinoline ligand of an iridium (Ir) complex is substituted by the cyclohexyl group to improve luminance efficiency and color purity. In addition, the phenylquinoline ligand of the IR complex is substituted by at least one selected from alkyl group, alkoxy group, halogen atom, trimethylsily group and tert-trifluoromethyl group to further improve luminance efficiency and color purity. The red phosphorescent compound is represented by following Formula 9.

[Formula 9]

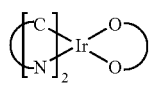

In the above Formula 9,

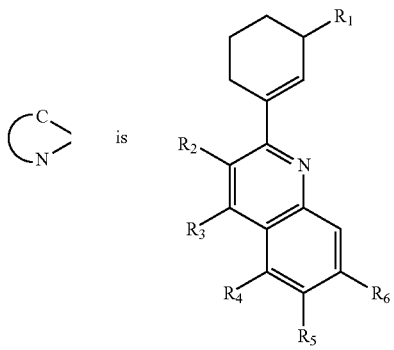

and R1 is selected from C1 to C6 substituted or non-substituted alkyl group and C1 to C6 substituted or non-substituted alkoxy group. Each of R2 to R6 is selected from hydrogen atom (H), C1 to C6 substituted or non-substituted alkyl group, C1 to C6 substituted or non-substituted alkoxy group, halogen atom, trimethylsily group and tert-trifluoromethyl. In addition, at least one of the R2 to R6 is selected from C1 to C6 substituted or non-substituted alkyl group, C1 to C6 substituted or non-substituted alkoxy group, halogen atom, trimethylsily group and tert-trifluoromethyl.

For example, the halogen atom includes fluorine (F), chlorine (Cl), bromine (Br) and iodine (I). The C1 to C6 alkyl group includes methyl, ethyl, n-propyl, i-propyl, n-butyl, i-butyl and t-butyl. The C1 to C6 alkoxy group includes methoxy, ethoxy, n-propoxy, i-propoxy, n-butoxy, i-butoxy and t-butoxy.

In addition, in the above formula 9,

as a right side structure of central iridium (Ir) is selected from the following Formulas 3-1 to 3-8. The structures of the above Formulas 3-1 to 3-8 are 2,4-pentanedione, 2,2,6,6-tetramethylheptane-3,5-dione, 1,3-propanedione, 1,3-butanedione, 3,5-heptanedione, 1,1,1-trifluoro-2,4-pentanedione, 1,1,1,5,5,5-hexafluoro-2,4-pentanedione and 2,2-dimethyl-3,5-hexanedione, respectively.

For example, the red phosphorescent compound represented by Formula 9 is selected from the following Formula 10.

[Formula 10]

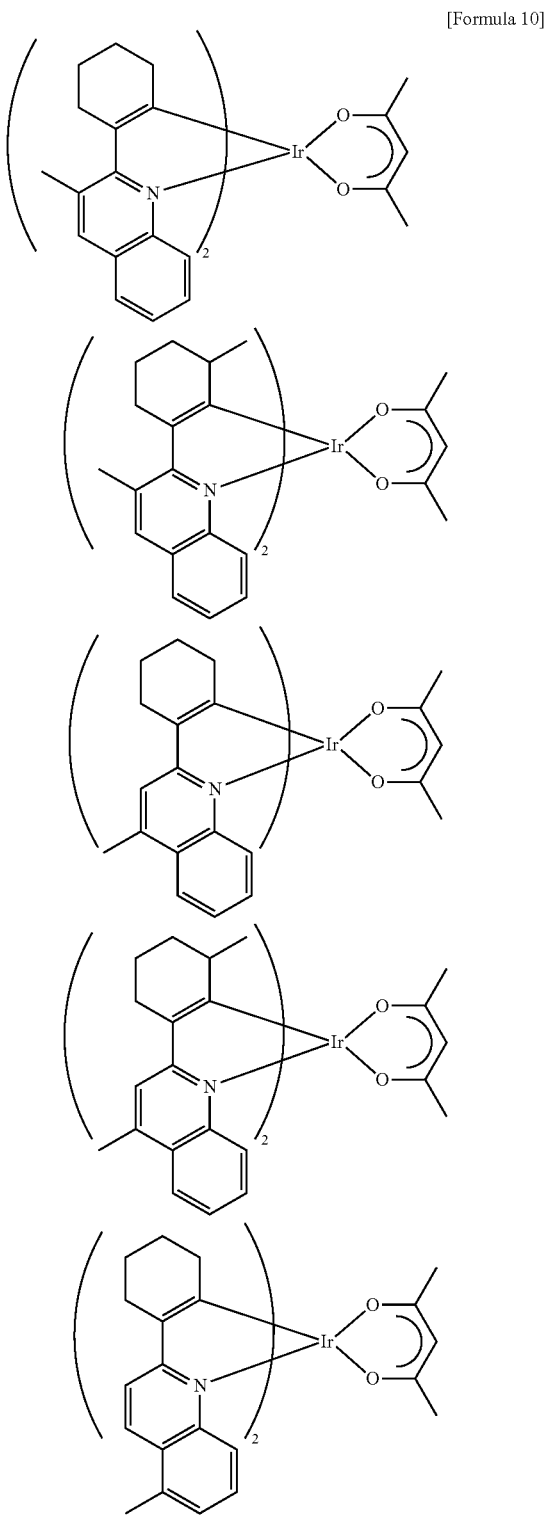

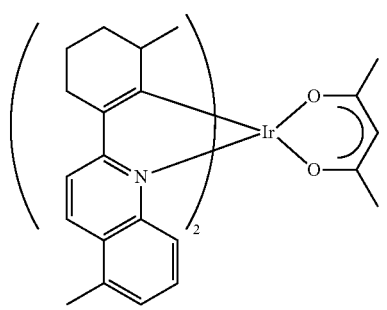
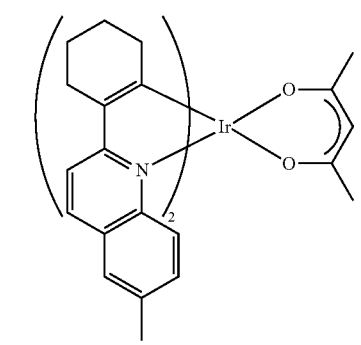
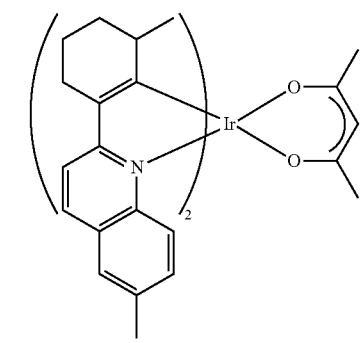
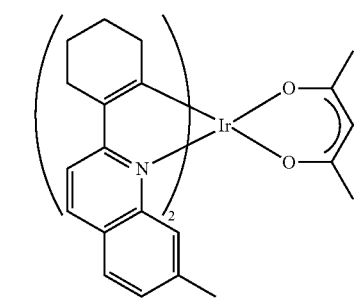
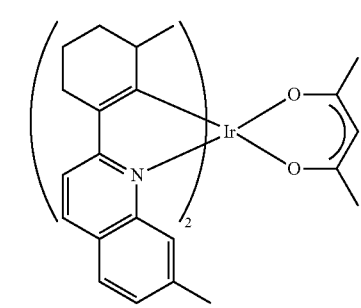
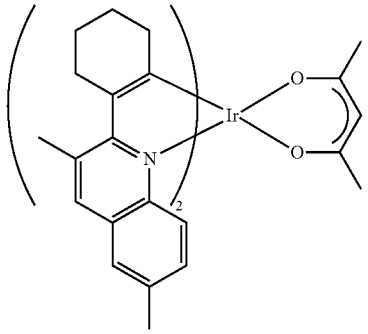
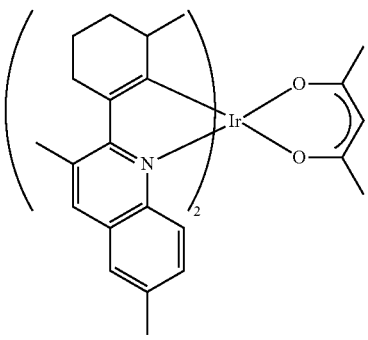
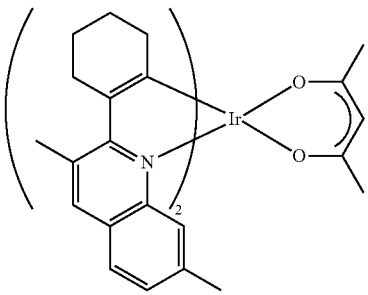
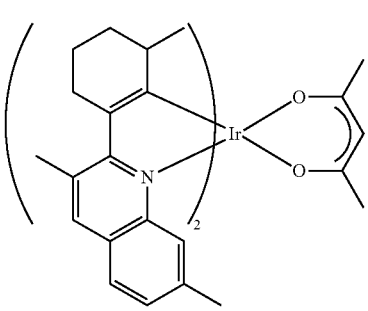
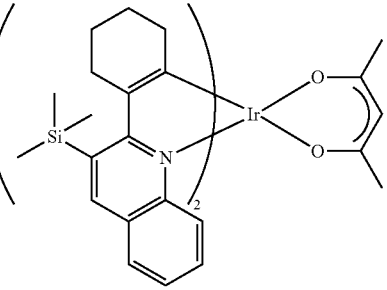

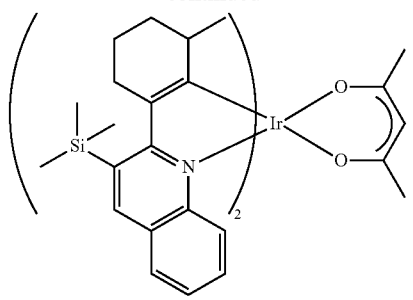
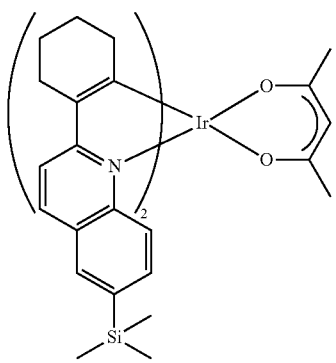
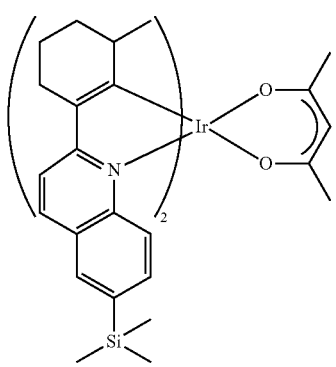
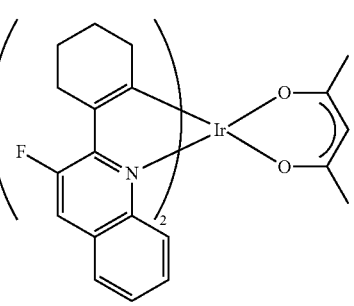
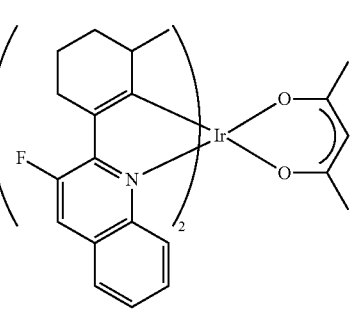
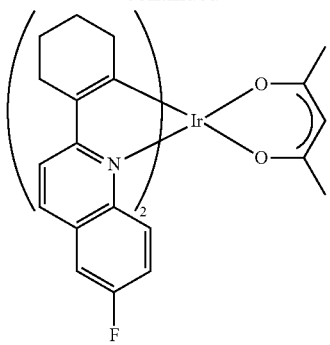
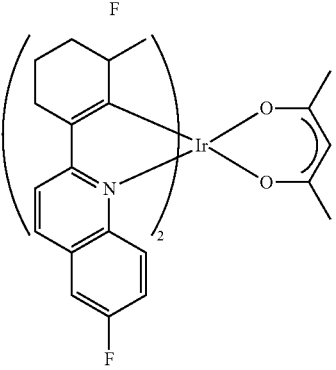
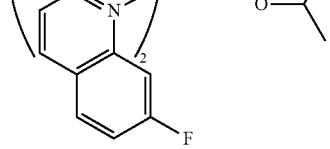
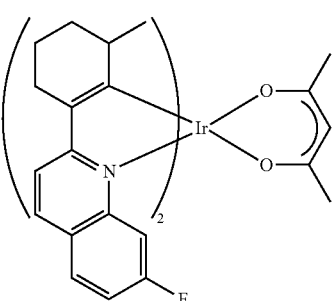
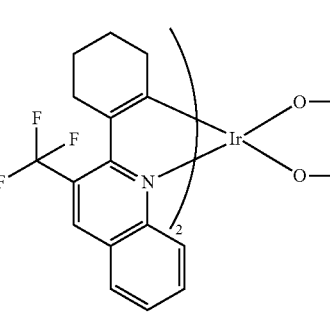

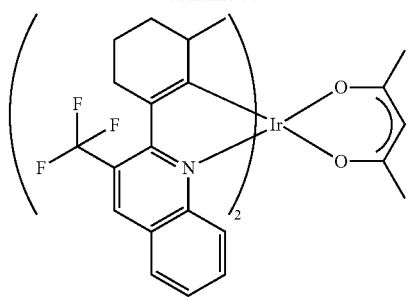
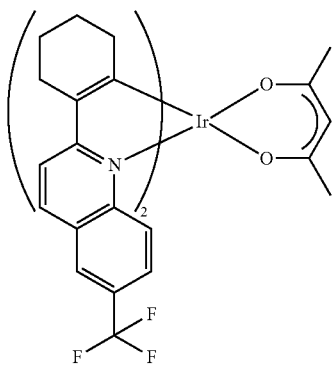
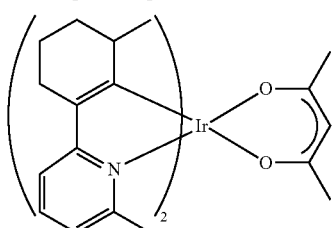
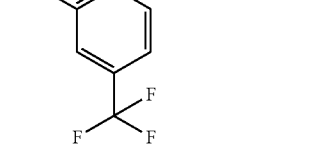
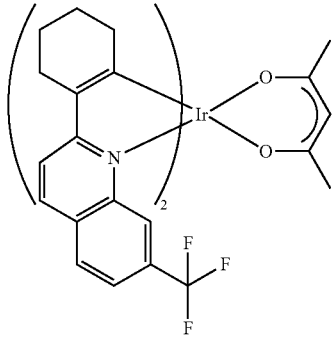
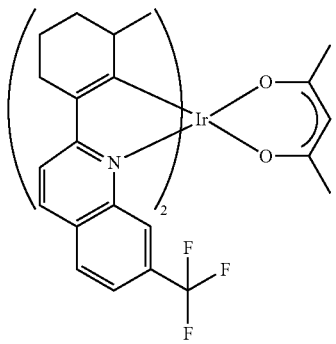
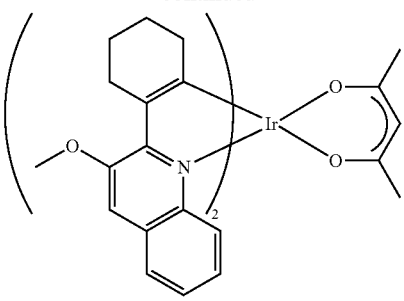
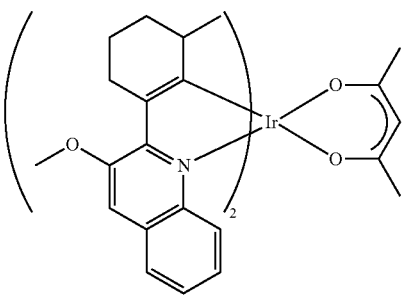
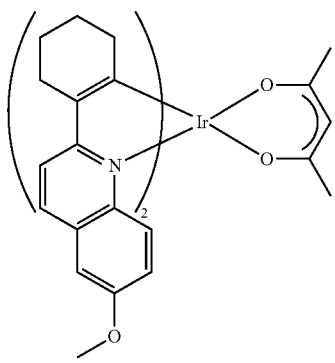
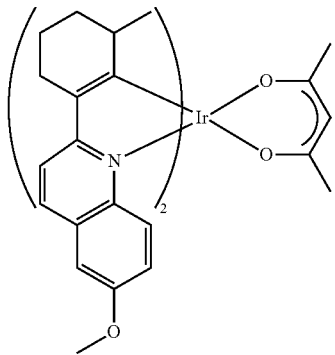
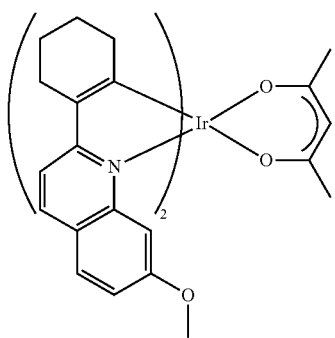

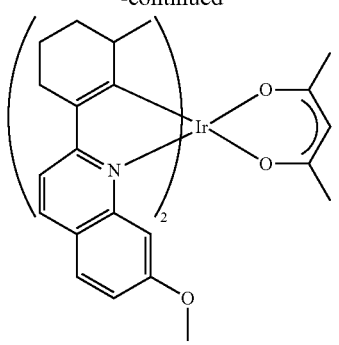
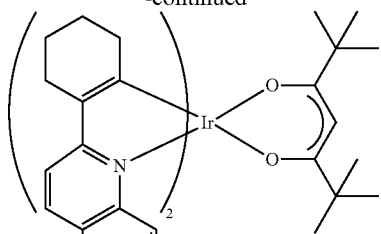
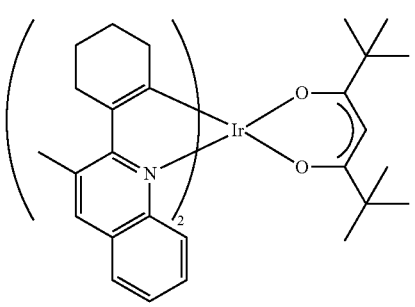
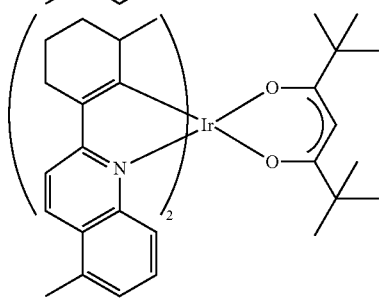
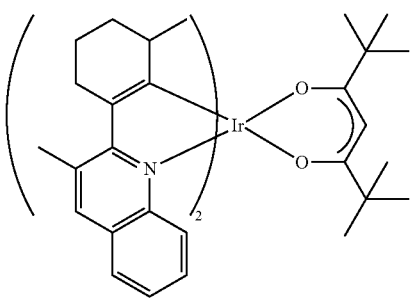
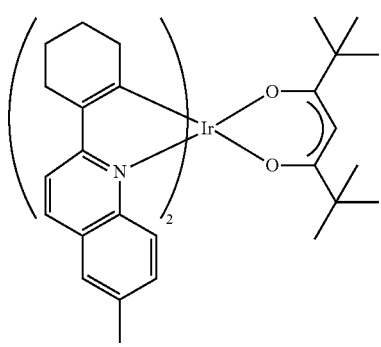
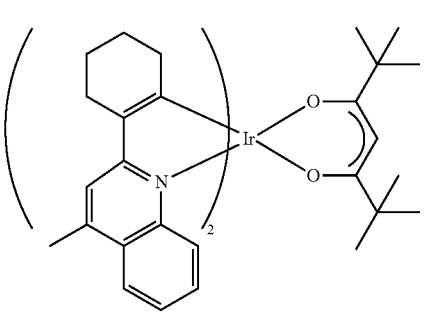
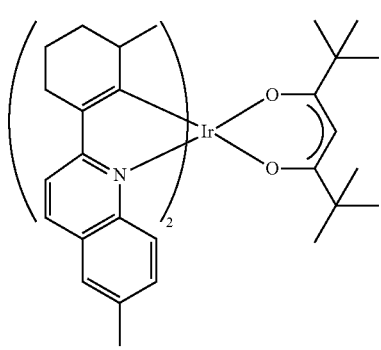
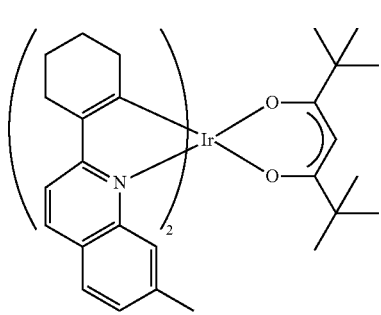

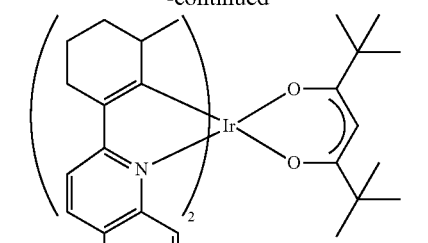
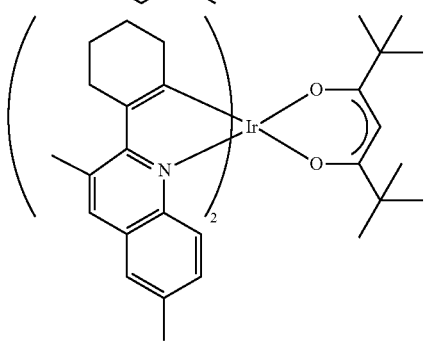
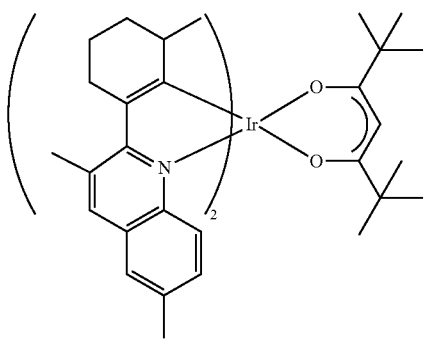
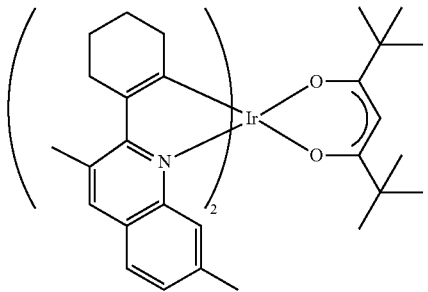
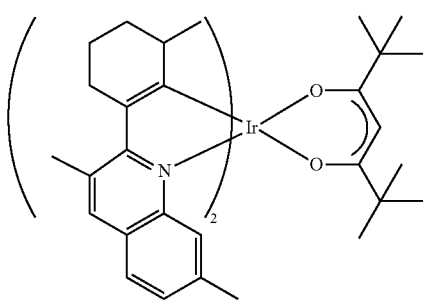
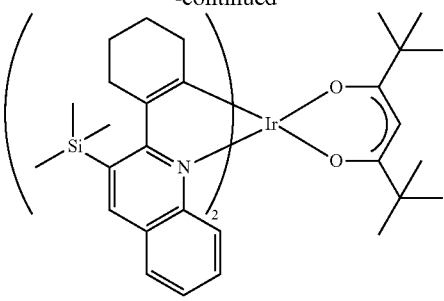
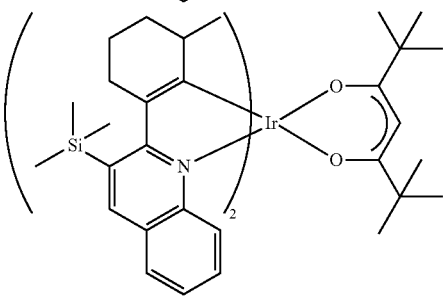
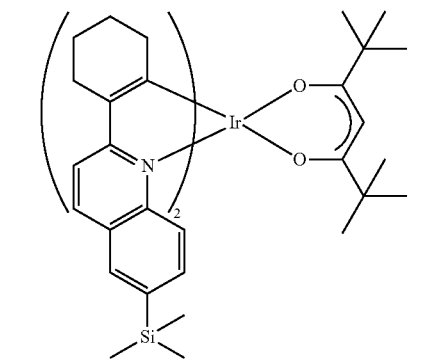
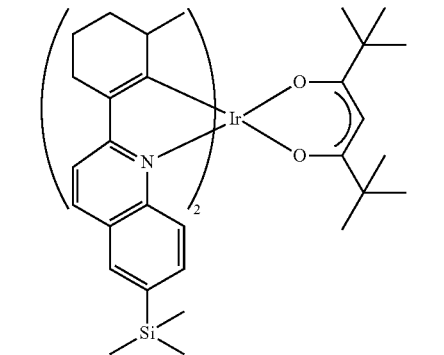
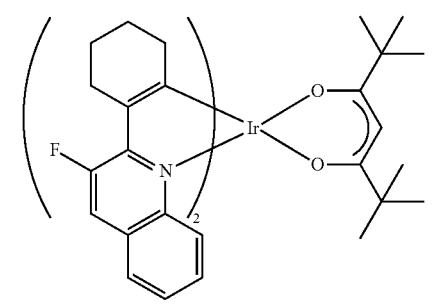

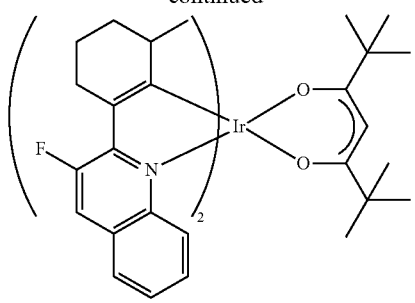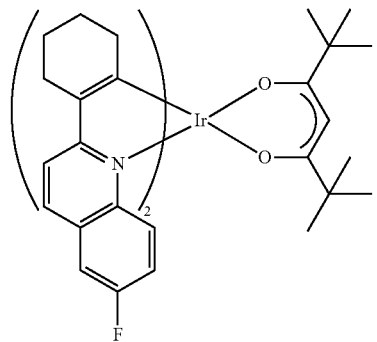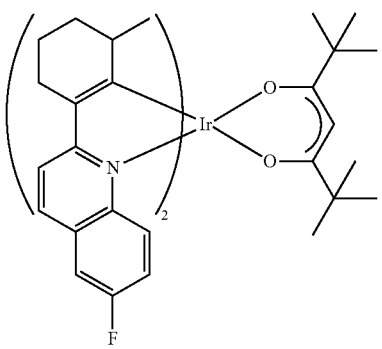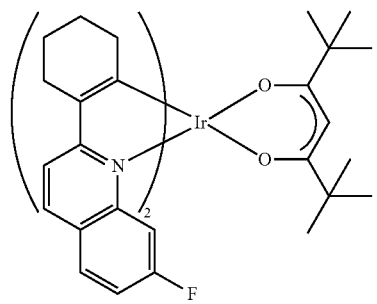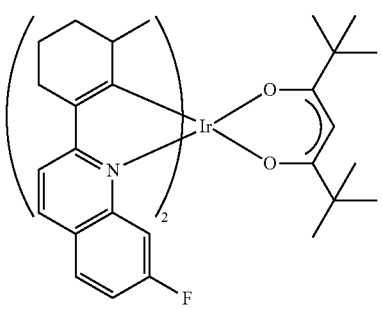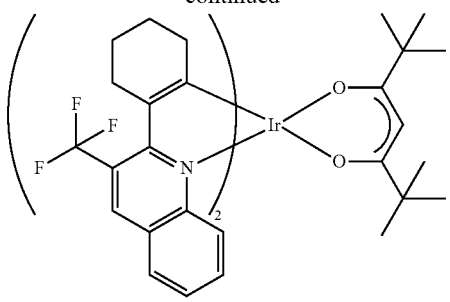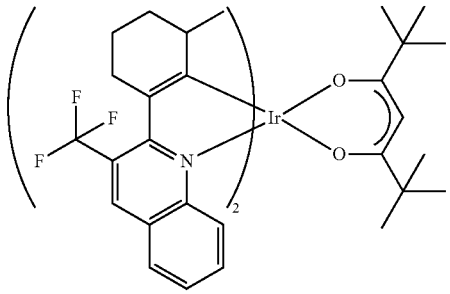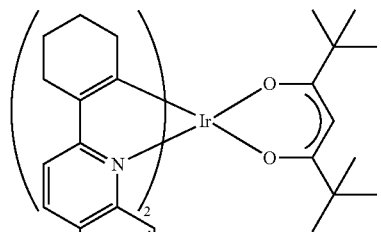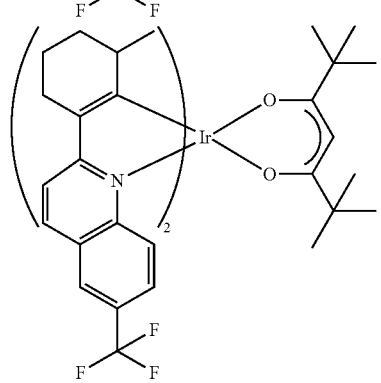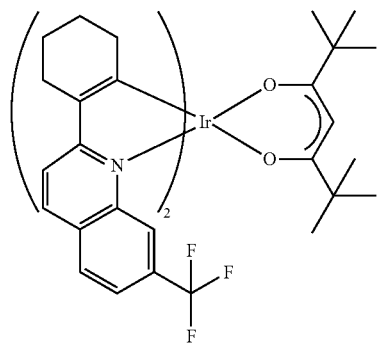

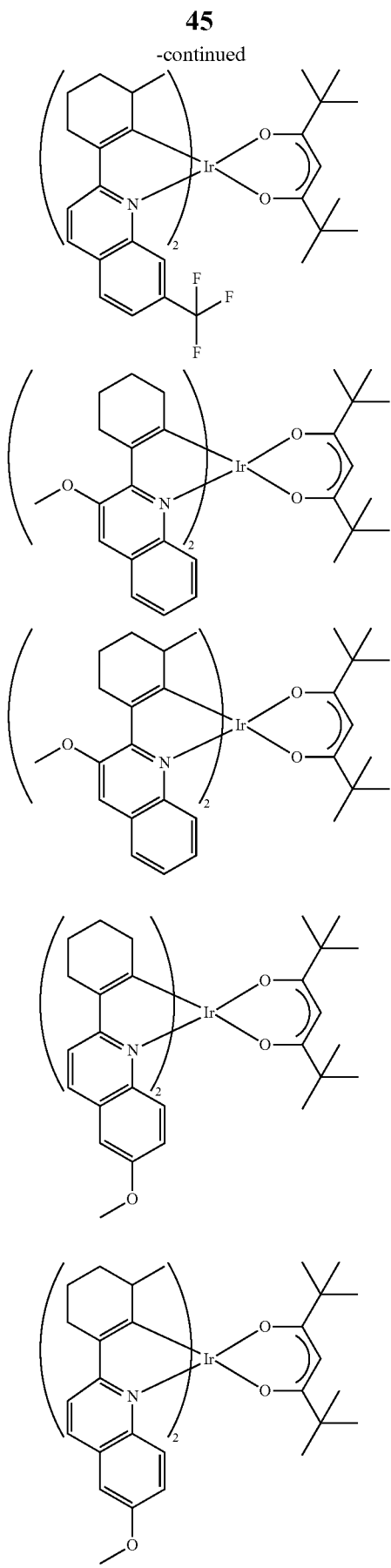

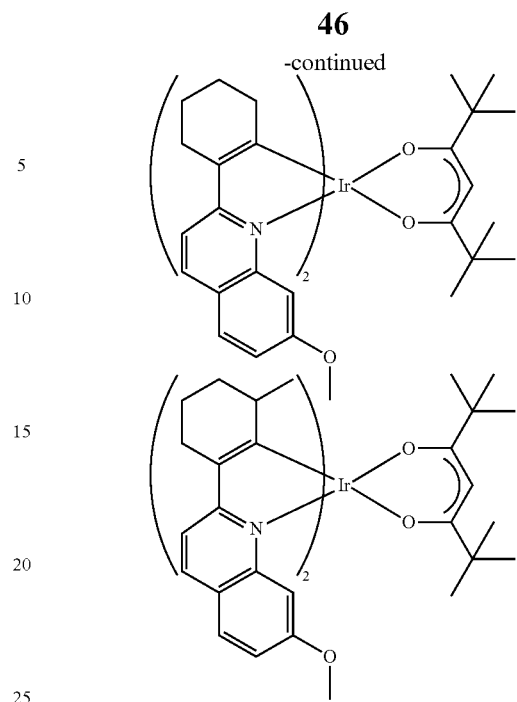

Synthesis

A synthesis example of the red phosphorescent compound represented by

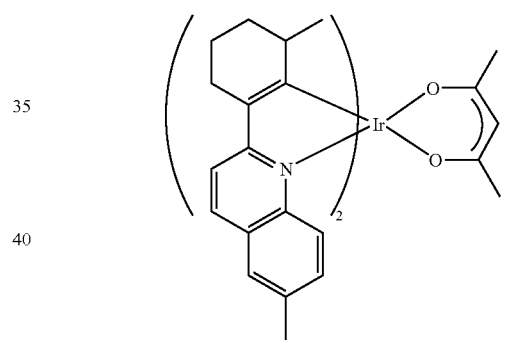

in the Formula 10 is explained. The red phosphorescent compound is iridium(III)bis{2-(3'-methylcyclohexenyl)-6-methylquinoline-N,C$^{2'}$}(2,4-pentanedionate-0,0).

1. Synthesis of 2-(3'-methylcyclohexanol)-6-methylquinoline 2-(3'-methylcyclohexanol)-6-methylquinoline is synthesized by following Reaction Formula 7.

[Reaction Formula 7]

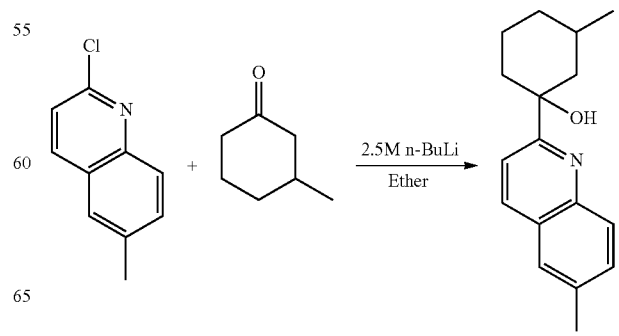

2-chloro-6-methyl quinoline (5 g, 0.03 mol) and diethylether (50 mL) are put in a two-neck round-bottom flask and stirred. After the resulting solution is cooled using a dry ice bath to about −78° C., 2.5M n-BuLi (12 mL, 0.03 mol) is dropped and stirred under a temperature of about 0° C. for 1 hour. Then, after the solution is cooled again using a dry ice bath to about −78° C., 3-methylcyclohexanone (5 g, 0.045 mol) is dropped and stirred under a room temperature for 6 hours. Next, 2N—HCl (50 mL) is added and stirred. Then, the resulting solution is extracted with methylenechloride, and then being distilled under reduced pressure such that 2-(3'-methylcyclohexanol)-6-methylquinoline (3.7 g, 56%) is yield.

2. Synthesis of 2-(3'-methylcyclohexenyl)-6-methylquinoline 2-(3'-methylcyclohexenyl 1)-6-methylquinoline is synthesized by following Reaction Formula 8.

[Reaction Formula 8]

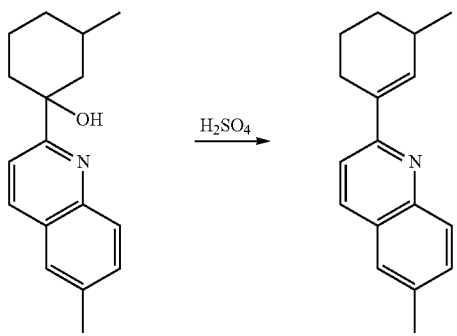

An aqueous solution of H2SO4 (10 mL) is added into 2-(3'-methylcyclohexanol)-6-methylquinoline at about 10° C., and then being stirred under a room temperature for 1 hour. The solution is stirred for about 30 minutes in iced water (50 g) and has a base property using 20% NaOH. The resulting solution is extracted with methylenechloride, and then being distilled under reduced pressure. The resulting residence is filtered by silica gel column and distilled under reduced pressure such that 2-(3'-methylcyclohexenyl)-6-methylquinoline (3.0 g) is yield.

3. Synthesis of chloro-bridged Ir dimer complex

Chloro-bridged Ir dimer complex is synthesized by following Reaction Formula 9.

[Reaction Formula 9]

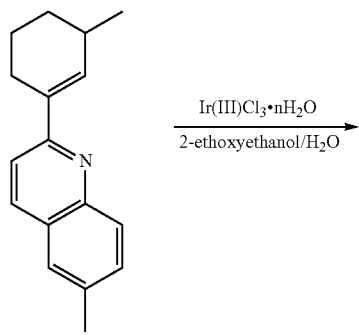

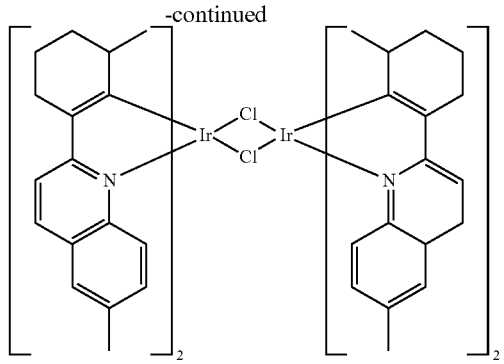

Iridium (III) chloride (5 mmol) and 2-(3'-methylcyclohexenyl)-6-methylquinoline (10 mmol) is put in a mixed solvent (30 mL), where a ratio of 2-ethoxyethanol to distilled water is 3:1. The mixture is refluxed for 24 hours, and water is added thereto. The resulting solid is filtered and washed by distilled water to yield chloro-bridged Ir dimer complex.

4. Synthesis of iridium(III) bis{2-(3'-methylcyclohexenyl)-6-methylquinoline-N,$C^{2'}$}(2,4-pentanedionate-0,0)

Iridium(III)bis{243'-methylcyclohexenyl)-6-methylquinoline-N,$C^{2'}$}(2,4-pentane dionate-0,0) is synthesized by following Reaction Formula 10.

[Reaction Formula 10]

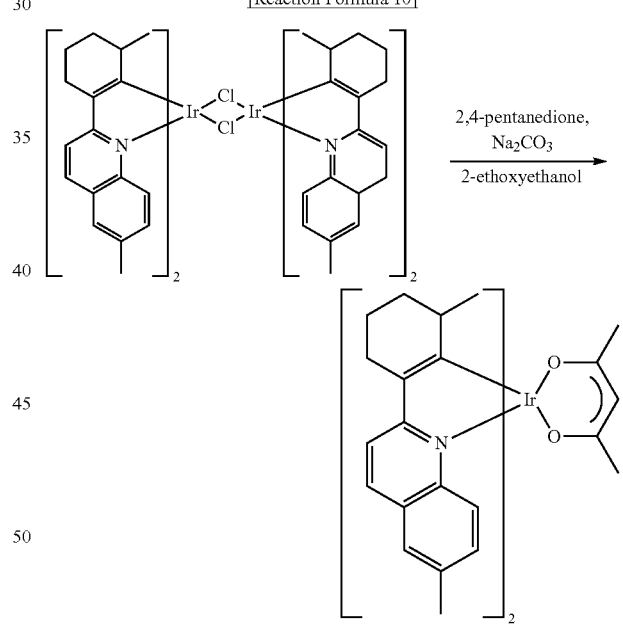

Chloro-bridged Ir dimer complex (1 mmol), 2,4-pentanedione (3 mmol) and sodium carbonate (Na₂CO₃) (6 mmol) is put in 2-ethoxyethanol (30 mL), and is refluxed for 24 hours. The resulted mixture is cooled to a room temperature, and then distilled water is added thereto. The mixture is filtered. The resulted solid is dissolved in dichloromethane, and then is filtered by silica gel column. By recrystallizing the solution with dichloromethane and methanol, the compound is yield.

Hereinafter, a detailed description will be made of preferred examples associated with the OELD according to the present invention. More specifically, the examples relate to an OELD including an emission material layer which uses the red phosphorescent compound of Formula 9 as a dopant.

EXAMPLES

Example 9

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including BAlq and

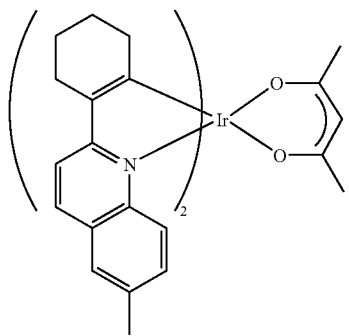

in the above Formula 10 as a dopant (about 5 weight %), Alq3 (about 300 angstroms), fluorolithium (LiF) (about 5 angstroms) and aluminum (Al) (about 1000 angstroms) are sequentially formed on the ITO layer such that an OELD is fabricated.

The OELD produces a brightness of 1270 cd/m² at an electric current of 0.9 mA and a voltage of 5.6 V. At this time, the X index and Y index of CIE color coordinates are 0.680 and 0.323, respectively, and the OELD has a lifetime of 5500 hours at 2000 cd/m². The lifetime is defined as the time taken before the luminance of the OELD decreases to half its initial value.

Example 10

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including BAlq and

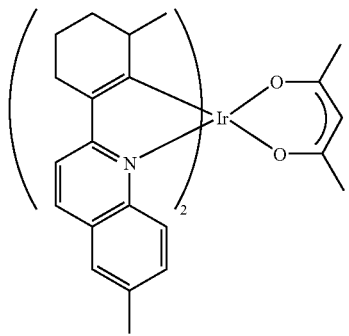

in the above Formula 10 as a dopant (about 5 weight %), Alq3 (about 300 angstroms), fluorolithium (LiF) (about 5 angstroms) and aluminum (Al) (about 1000 angstroms) are sequentially formed on the ITO layer such that an OELD is fabricated.

The OELD produces a brightness of 1221 cd/m² at an electric current of 0.9 mA and a voltage of 5.5 V. At this time, the X index and Y index of CIE color coordinates are 0.684 and 0.322, respectively, and the OELD has a lifetime of 5000 hours at 2000 cd/m².

Example 11

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including BAlq and

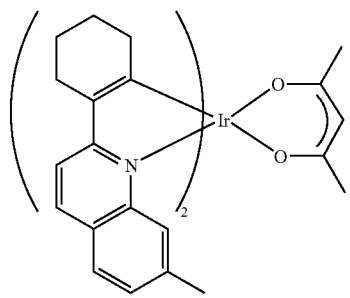

in the above Formula 10 as a dopant (about 5 weight %), Alq3 (about 300 angstroms), fluorolithium (LiF) (about 5 angstroms) and aluminum (Al) (about 1000 angstroms) are sequentially formed on the ITO layer such that an OELD is fabricated.

The OELD produces a brightness of 1301 cd/m² at an electric current of 0.9 mA and a voltage of 5.3 V. At this time, the X index and Y index of CIE color coordinates are 0.681 and 0.332, respectively, and the OELD has a lifetime of 6500 hours at 2000 cd/m².

Example 12

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including BAlq and

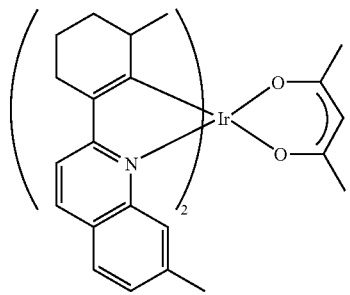

in the above Formula 10 as a dopant (about 5 weight %), Alq3 (about 300 angstroms), fluorolithium (LiF) (about 5 angstroms) and aluminum (Al) (about 1000 angstroms) are sequentially formed on the ITO layer such that an OELD is fabricated.

The OELD produces a brightness of 1254 cd/m² at an electric current of 0.9 mA and a voltage of 5.4 V. At this time, the X index and Y index of CIE color coordinates are 0.685 and 0.331, respectively, and the OELD has a lifetime of 6000 hours at 2000 cd/m².

Comparative Example 3

An ITO layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including BAlq and RD-1 represented by the above Formula 1-1 as a dopant (about 7 weight %), Alq3 (about 300 angstroms), LiF (about 5 angstroms) and Al (about 1000 angstroms) are sequentially formed on the ITO layer such that an OELD is fabricated.

The OELD produces a brightness of 1173 cd/m² at an electric current of 0.9 mA and a voltage of 6.0 V. At this time, the X index and Y index of CIE color coordinates are 0.606 and 0.375, respectively, and the OELD has a lifetime of 4000 hours at 2000 cd/m².

Comparative Example 4

An ITO layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including BAlq and RD-2 represented by the above Formula 1-2 as a dopant (about 7 weight %), Alq3 (about 300 angstroms), LiF (about 5 angstroms) and Al (about 1000 angstroms) are sequentially formed on the ITO layer such that an OELD is fabricated.

The OELD produces a brightness of 780 cd/m² at an electric current of 0.9 mA and a voltage of 7.5 V. At this time, the X index and Y index of CIE color coordinates are 0.659 and 0.329, respectively, and the OELD has a lifetime of 6000 hours at 2500 cd/m².

As mentioned above, BAlq as a host is used for an emission material layer. However, the emission material layer may be formed of other materials. For example, Al metallic complex, zinc (Zn) metallic complex or CBP may be used for the emission material layer. CBP is a carbazole derivitive, such as 4-4'-N—N'-dicarbazole-1-1'-biphenyl, and represented by the above Formula 6. For example, the dopant is added into a host material by about 0.1 to 50 weight %.

In addition, a ligand of the Al metallic complex or the Zn metallic complex may be selected from quinolinyl, biphenynyl, isoquinolinyl, phenylnyl, methylquinolinyl, dimethylquinolinyl, and dimethyl isoquinolinyl.

The OELD fabricated in Examples 9 to 12 and Comparative Examples 3 and 4 is evaluated for efficiency, brightness, lifetime, and so on. A voltage has a dimension of [V], an electric current has a dimension of [mA], a brightness has a dimension of [cd/m2], a current efficiency has a dimension of [cd/A], a power efficiency has a dimension of [lm/W], an internal quantum efficiency has a dimension of [%], and a lifetime has a dimension of [hour]. The evaluated results are shown in Table 3.

TABLE 3

| | voltage | Electric current | Brightness | Current efficiency | Power efficiency | Internal quantum efficiency | CIE (X) | CIE (Y) | lifetime |
|---|---|---|---|---|---|---|---|---|---|
| Ex. 9 | 5.6 | 0.9 | 1270 | 12.7 | 7.5 | 18.7 | 0.680 | 0.323 | 5500 |
| Ex. 10 | 5.5 | 0.9 | 1221 | 12.2 | 7.3 | 18.3 | 0.684 | 0.322 | 5000 |
| Ex. 11 | 5.3 | 0.9 | 1301 | 13.0 | 8.1 | 19.1 | 0.681 | 0.332 | 6500 |
| Ex. 12 | 5.4 | 0.9 | 1254 | 12.5 | 7.7 | 18.5 | 0.685 | 0.331 | 6000 |
| Com. Ex. 3 | 6.0 | 0.9 | 1173 | 11.7 | 6.2 | 12.0 | 0.606 | 0.375 | 4000 |
| Com. Ex. 4 | 7.5 | 0.9 | 780 | 7.8 | 3.3 | 10.4 | 0.659 | 0.329 | 2500 |

As shown in Table 3, the OELD in Examples 9 to 12 has high color purity and high internal quantum efficiency. Accordingly, the OELD according to the present invention has improved luminescence efficiency. As a result, when the red phosphorescent compound of the present invention as a dopant for an emission material layer of an OELD, the OELD has high color purity, high brightness and high luminescence efficiency. The OELD can be driven by a relatively low power, power consumption can be reduced.

Figure 2:
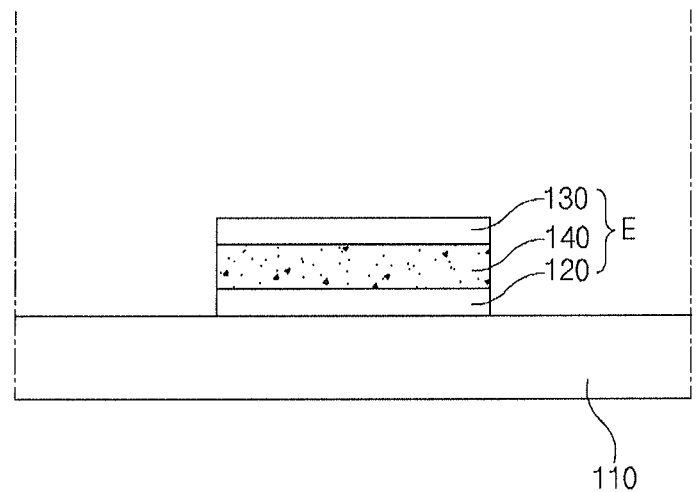
FIG. 2 is a schematic cross-sectional view of an OELD according to the present invention.

FIG. 2 is a schematic cross-sectional view of an OELD according to the present invention. In FIG. 2, an OELD includes a first substrate 101, a second substrate (not shown) facing the first substrate 101, and an organic electroluminescent diode E on the first substrate 101. Namely, the organic electroluminescent diode E is positioned between the first substrate 101 and the second substrate.

The organic electroluminescent diode E includes a first electrode 120 as an anode, a second electrode 130 as a cathode, and an organic emitting layer 140 between the first and second electrodes 120 and 130. The first electrode 120 being closer to the first substrate 110 than the second electrode 130 is shown. Alternatively, the second electrode 130 may be closer to the first substrate 110 than the first electrode 120.

The first electrode 120 is formed of a material having a large work function. For example, the first electrode 120 may be formed of ITO. The second electrode 130 is formed of a material having a small work function. For example, the second electrode 130 may be formed of one of Al and Al alloy (AlNd).

The organic emitting layer 140 includes red, green and blue organic emitting patterns. In this case, the red emission pattern of the EML includes a host material, which is capable of transporting an electron and a hole, and the red phosphorescent compound according to the present invention as a dopant. The red phosphorescent compound according to the present invention is represented by the above Formulas 2, 7 and 9. The red phosphorescent compound as a dopant is added with a range of about 0.1 weight % to about 50 weight % with respect to a total weight of a material in the red emission pattern.

Although not shown, to maximize luminescence efficiency, the organic emission layer 140 has a multiple-layered structure. For example, a hole injection layer (HIL), a hole transporting layer (HTL), an emitting material layer (EML), an electron transporting layer (ETL) and an electron injection layer (EIL) are stacked on the first electrode 120.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A red phosphorescent composition, comprising:
a host material being capable of transporting an electron or a hole; and
a dopant material represented by following Formula 1:

[Formula 1]

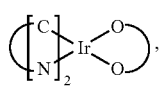

wherein the  is one of R1 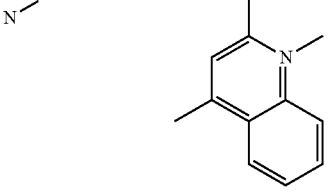 and

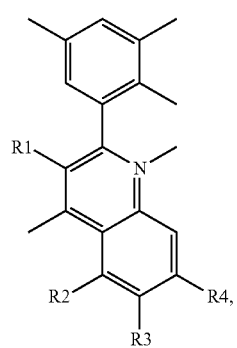

and each of R1 and R3 is one of the group consisting of hydrogen atom (H), C1 to C6 substituted or non-substituted alkyl group, C1 to C6 substituted or non-substituted alkoxy group, and halogen atom, and wherein R2 and R4 each is methyl.

2. The composition according to claim 1, wherein the C1 to C6 alkyl is one of the group consisting of methyl, ethyl, n-propyl, i-propyl, n-butyl, i-butyl and t-butyl.

3. The composition according to claim 1, wherein the C1 to C6 alkoxy is one of the group consisting of methoxy, ethoxy, n-propoxy, i-propoxy, n-butoxy, i-butoxy and t-butoxy.

4. The composition according to claim 1, wherein the dopant material has a weight % of about 0.1 to about 50 with respect to a total weight of the composition.

5. The composition according to claim 1, wherein the host material is one of the group consisting of aluminum(III)bis (2-methyl-8-quinolinato)4-phenylphenolate (BAlq), Al metal complex, Zn metal complex and carbazole derivatives.

6. The composition according to claim 5, wherein the carbazole derivatives are 4,4'-N,N'-dicarbazole-biphenyl (CBP).

7. The composition according to claim 1, wherein the

is one of 2,4-pentanedione, 2,2,6,6-tetramethylheptane-3,5-dione, 1,3-propanedione, 1,3-butanedione, 3,5-heptanedione, 1,1,1-trifluoro-2,4-pentanedione, 1,1,1,5,5,5-hexafluoro-2,4-pentanedione and 2,2-dimethyl-3,5-hexanedione.

8. An organic electroluminescent device, comprising:
a first substrate;
a thin film transistor on the first substrate;
a second substrate facing the first substrate; and
an organic luminescent diode electrically connected to the thin film transistor and including a first electrode, a second electrode facing the first electrode and an organic emission layer disposed between the first and second electrodes, a red phosphorescent composition of the organic emission layer including:
a host material being capable of transporting an electron or a hole; and
a dopant material represented by following Formula 1:

[Formula 1]

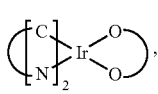

wherein the  is one of R1  and

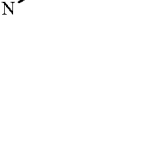
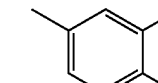
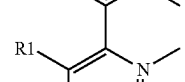
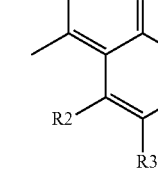

and each of R1 and R3 is one of the group consisting of hydrogen atom (H), C1 to C6 substituted or non-substituted alkyl group, C1 to C6 substituted or non-substituted alkoxy group, and halogen atom, and wherein R2 and R4 each is methyl.

* * * * *